(12) United States Patent
Remmelgas et al.

(10) Patent No.: US 8,578,933 B2
(45) Date of Patent: Nov. 12, 2013

(54) ENTRAINING POWDER IN AN AIRFLOW

(75) Inventors: Johan Remmelgas, Torslanda (SE); Per Arne Kjellgren, Asker (NO); Orest Lastow, Lund (SE); Mårten Svensson, Södra Sandby (SE)

(73) Assignee: AstraZeneca AB, Södertälje (SE)

( * ) Notice: Subject to any disclaimer, the term of this patent is extended or adjusted under 35 U.S.C. 154(b) by 1079 days.

(21) Appl. No.: 12/496,525

(22) Filed: Jul. 1, 2009

(65) Prior Publication Data
US 2010/0051027 A1    Mar. 4, 2010

Related U.S. Application Data

(63) Continuation-in-part of application No. PCT/SE2008/051488, filed on Dec. 18, 2008.

(60) Provisional application No. 61/015,383, filed on Dec. 20, 2007.

(51) Int. Cl.
*A61M 15/00* (2006.01)
*B65D 83/06* (2006.01)

(52) U.S. Cl.
USPC .................................................... 128/203.15

(58) Field of Classification Search
USPC ............. 128/203.15, 203.19, 203.23, 203.21, 128/203.24, 203.12, 203.14, 203.25, 203.29
See application file for complete search history.

(56) References Cited

U.S. PATENT DOCUMENTS

| | | |
|---|---|---|
| 3,872,970 A | 3/1975 | Edison |
| 3,948,264 A | 4/1976 | Wilke et al. |
| 4,210,140 A | 7/1980 | James et al. |
| 4,446,862 A | 5/1984 | Baum et al. |
| 4,849,606 A | 7/1989 | Martens et al. |
| 4,860,740 A | 8/1989 | Kirk et al. |
| 4,946,038 A | 8/1990 | Eaton |

(Continued)

FOREIGN PATENT DOCUMENTS

| AU | 651910 B2 | 3/1993 |
|---|---|---|
| DE | 102005046645 | 7/2006 |

(Continued)

OTHER PUBLICATIONS

Atvars, K. et al., "Experimental and Computational Investigation of an 'Open' Transonic Cavity Flow" *Proceedings of the Institution of Mechanical Engineers, Part G: Journal of Aerospace Engineering* 223(4):357-368 (Apr. 1, 2009).

(Continued)

*Primary Examiner* — (Jackie) Tan-Uyen T. Ho
*Assistant Examiner* — Peter S Vasat
(74) *Attorney, Agent, or Firm* — Finnegan, Henderson, Farabow, Garrett & Dunner, LLP

(57) ABSTRACT

A device for inhalation of at least one air stream carrying a dose of medicament powder. The device comprises a powder-containing cavity which opens into a flow passage. The flow passage is arranged to direct an inhalation air flow across the cavity opening. A circulating flow is thereby induced in the cavity by the phenomenon of shear driven cavity flow. Powder is entrained in the circulating flow and deaggregated before exiting the cavity and becoming entrained in the flow of air along the flow passage.

35 Claims, 9 Drawing Sheets

(56) References Cited

U.S. PATENT DOCUMENTS

| | | | |
|---|---|---|---|
| 5,042,472 A | 8/1991 | Bunin | |
| 5,383,850 A | 1/1995 | Schwab et al. | |
| 5,469,843 A | 11/1995 | Hodson | |
| 5,660,169 A | 8/1997 | Källstrand et al. | |
| 5,694,920 A | 12/1997 | Abrams et al. | |
| 6,006,747 A | 12/1999 | Eisele et al. | |
| 6,102,035 A * | 8/2000 | Asking et al. | 128/203.15 |
| 6,234,169 B1 | 5/2001 | Bulbrook et al. | |
| 6,575,160 B1 * | 6/2003 | Volgyesi | 128/203.15 |
| 6,637,431 B2 | 10/2003 | Ekelius et al. | |
| 6,655,381 B2 | 12/2003 | Keane et al. | |
| 6,840,239 B2 | 1/2005 | Myrman | |
| 6,871,647 B2 * | 3/2005 | Allan et al. | 128/203.21 |
| 6,948,494 B1 | 9/2005 | Snow | |
| 7,395,821 B2 | 7/2008 | Lulla et al. | |
| 7,448,379 B2 * | 11/2008 | Yamashita et al. | 128/203.15 |
| 7,533,668 B1 * | 5/2009 | Widerstrom | 128/203.15 |
| 7,810,495 B2 | 10/2010 | Gumaste | |
| 2003/0015195 A1 | 1/2003 | Haaije De Boer et al. | |
| 2003/0192539 A1 | 10/2003 | Myrman | |
| 2004/0069303 A1 | 4/2004 | Brown et al. | |
| 2004/0107963 A1 | 6/2004 | Finlay et al. | |
| 2004/0123864 A1 | 7/2004 | Hickey et al. | |
| 2006/0237010 A1 | 10/2006 | De Boer et al. | |
| 2007/0131576 A1 | 6/2007 | Ehling et al. | |
| 2007/0151562 A1 | 7/2007 | Jones et al. | |
| 2007/0181123 A1 | 8/2007 | Houzego | |
| 2008/0001008 A1 | 1/2008 | Thoemmes et al. | |
| 2008/0127974 A1 | 6/2008 | Lastow | |
| 2008/0142006 A1 | 6/2008 | Bulbrook | |
| 2008/0314384 A1 * | 12/2008 | Harris et al. | 128/203.15 |
| 2009/0084379 A1 | 4/2009 | Goeckner et al. | |
| 2009/0114220 A1 | 5/2009 | Wachtel et al. | |
| 2010/0000529 A1 | 1/2010 | Prime et al. | |
| 2010/0300442 A1 | 12/2010 | Houzego et al. | |
| 2011/0036348 A1 | 2/2011 | Lastow et al. | |
| 2011/0083667 A1 | 4/2011 | Briant et al. | |
| 2011/0226243 A1 | 9/2011 | Lastow et al. | |

FOREIGN PATENT DOCUMENTS

| | | |
|---|---|---|
| EP | 1318849 | 9/2001 |
| EP | 1173368 | 6/2005 |
| EP | 1844806 | 10/2007 |
| EP | 1 769 818 B1 | 11/2009 |
| GB | 1 472 650 | 5/1977 |
| GB | 1 502 150 | 2/1978 |
| GB | 1 520 062 | 8/1978 |
| GB | 1 521 000 | 8/1978 |
| GB | 2264237 | 2/1992 |
| GB | 2401548 | 11/2004 |
| WO | WO 92/04069 | 3/1992 |
| WO | WO 97/25086 A2 | 7/1997 |
| WO | WO 99/36116 | 7/1999 |
| WO | WO 0053248 | 9/2000 |
| WO | WO 0064779 | 11/2000 |
| WO | WO 03103563 | 12/2003 |
| WO | WO 2005030305 | 4/2005 |
| WO | WO 2005/081977 | 9/2005 |
| WO | WO 2006/118527 A1 | 11/2006 |
| WO | WO 2007/144614 A1 | 12/2007 |
| WO | WO 2008/110809 | 9/2008 |
| WO | WO 2009/008832 A1 | 1/2009 |
| WO | WO 2009/152477 A2 | 12/2009 |
| WO | WO 2011/002406 A1 | 1/2011 |

OTHER PUBLICATIONS

International Search Report and Written Opinion issued in International Patent Application No. PCT/SE2008/051488; Date of Mailing: Mar. 10, 2009.

International Search Report and Written Opinion issued in International Patent Application No. PCT/SE2008/051490; Date of Mailing: Mar. 11, 2009.

International Search Report and Written Opinion issued in International Patent Application No. PCT/SE2010/050749; Date of Mailing: Oct. 4, 2010.

Ukeiley, L. et al., "Velocity and surface pressure measurements in an open cavity" *Experiments in Fluids* 38:656-671 (2005).

Zhang, X., "Compressible Cavity Flow Oscillation due to Shear Layer Instabilities and Pressure Feedback" *AIAA Journal* 33(8):1404-1411 (Aug. 1995).

U.S. Appl. No. 12/940,683, filed Nov. 5, 2010 by Lastow et al.: Notice of Allowance, dated Dec. 9, 2011.

U.S. Appl. No. 12/940,683, filed Nov. 5, 2010 by Lastow et al.: Office Action, dated Jul. 15, 2011.

U.S. Appl. No. 12/940,683, filed Nov. 5, 2010 by Lastow et al.: Office Action, dated May 26, 2011.

\* cited by examiner

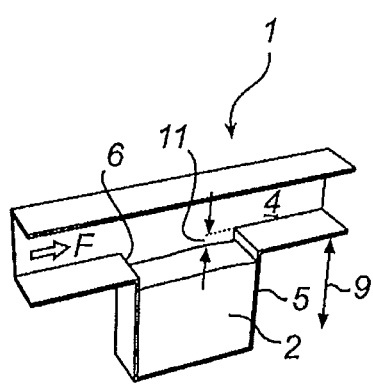
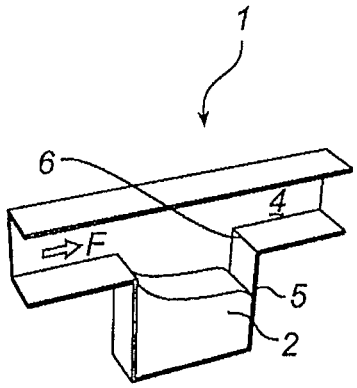
Fig. 3a   Fig. 3b
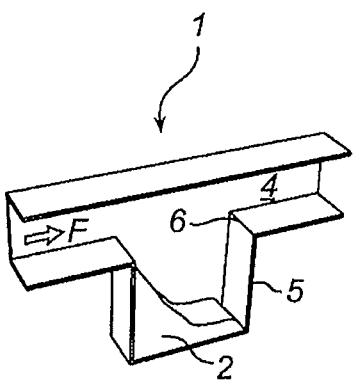
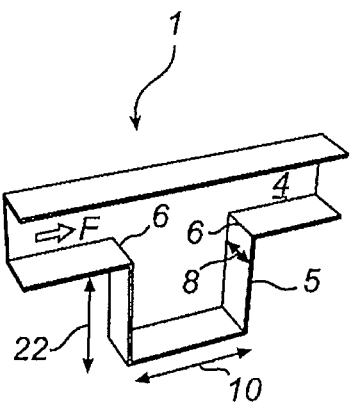
Fig. 3c   Fig. 3d
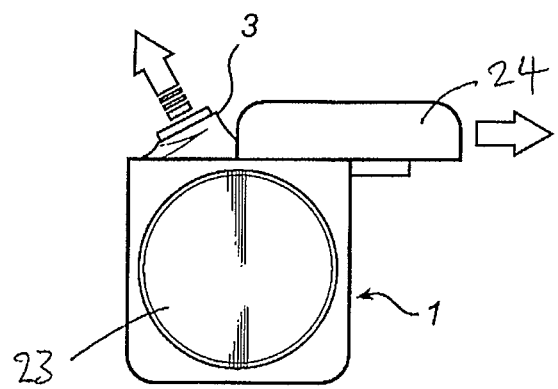
Fig. 4

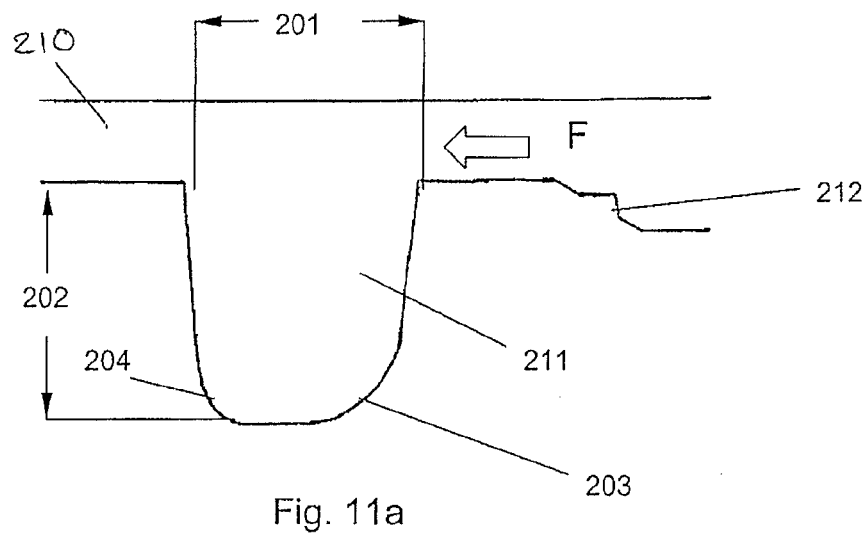
Fig. 11a
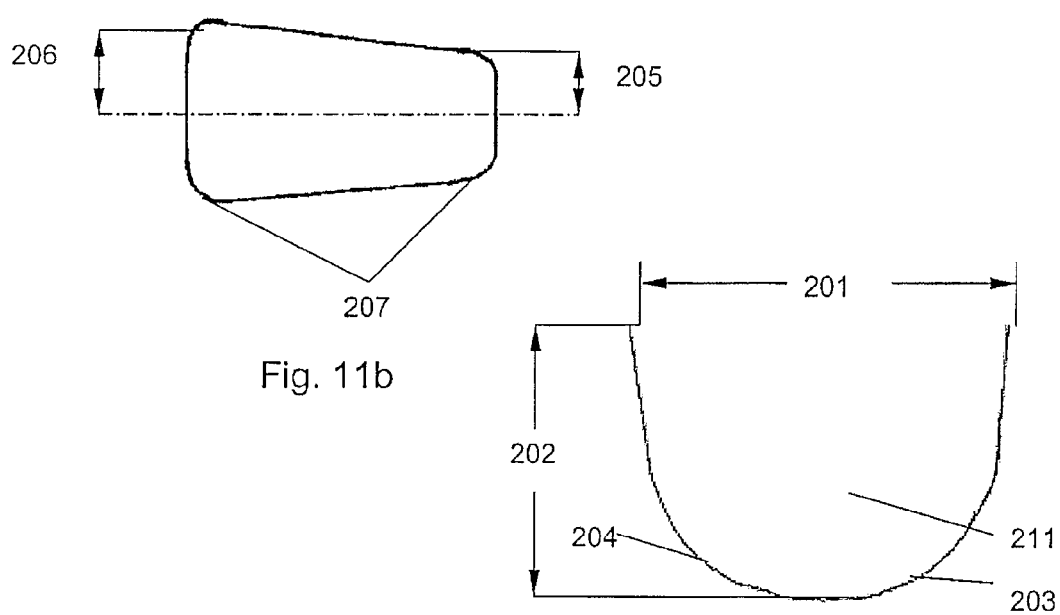
Fig. 11b
Fig. 11c
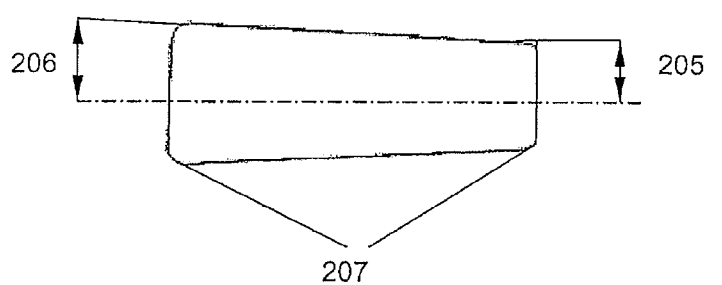
Fig. 11d

ENTRAINING POWDER IN AN AIRFLOW

CROSS-REFERENCE TO RELATED APPLICATIONS

This application is a continuation-in-part application of and claims priority to PCT Application Serial No. PCT/SE2008/051488, filed on Dec. 18, 2008, which claims priority to U.S. Ser. No. 61/015,383 filed on Dec. 20, 2007.

TECHNICAL FIELD

The present invention relates to a device and method for entraining in an airflow a medicament powder contained in a cavity. The present invention also relates to a medical dispenser that includes a powder-containing cavity.

BACKGROUND

There are many devices for administering powdered medicaments to the lungs, which employ propellants, such as compressed gases, e.g. air, or liquefied gas propellants, to dispense and disperse the medicament.

There are also a number of known breath actuated inhalation devices for administering powdered medicaments to the lungs, which have mouthpieces through which the medicament is inhaled. British Patent Specification Nos. 1 521 000, 1 520 062, 1 472 650 and 1 502 150 disclose devices where a capsule is inserted into the device, which mitigates spillage of medicament prior to inhalation. Access to the medicament is gained by piercing the capsule or cutting it in half inside the dispensing device. On inhalation the air flows into or through the capsule and the powder within is released into the air stream and flows towards the mouth.

U.S. Pat. No. 4,210,140 discloses a device in which access to the powdered medicament is gained by pulling the halves of the capsule apart so that the medicament is emptied to a suitable position for entrainment in the airflow caused by inhalation.

U.S. Pat. No. 6,655,381 relates to a pre-metered dose assembly for consistently supplying precise doses of medicament for a breath-actuated dry powder inhaler. The assembly includes a cap defining a dry powder delivery passageway for providing air to a dry powder supply port of a swirl chamber of a breath-actuated dry powder inhaler, and a magazine including a plurality of reservoirs for holding pre-metered doses of dry powder. One of the magazine and the cap is movable with respect to the other of the magazine and the cap for sequentially positioning the reservoirs within the delivery passageway of the cap. A breath-induced low pressure at an outlet port of the inhaler causes an airflow through the dry powder delivery passageway of the assembly and into the dry powder supply port that entrains dry powder from the reservoir positioned in the passageway for inhalation by a patient using the inhaler. The passageway is provided with a venturi in the passageway by the reservoir to create a flow through the reservoir and bring the powder there from.

U.S. Pat. No. 4,446,862 to Baum et al. describes an inhaler device in which access to the powdered medicament is gained by pulling the halves of a capsule apart, leaving the lower half of the capsule retained in an upright position in the device, with its open end flush with the lower surface of a disc shaped inhalation chamber. Spaced around half the circumference of the chamber are a number of air inlets and, opposite these, a larger air outlet leading to a mouthpiece. On inhalation, air is drawn through the chamber and across the open mouth of the capsule. It is stated that this may create a resonance effect in the capsule, similar to the effect which causes a sound to be produced by blowing across the opening of a bottle.

US published patent application number 2009114220 to Boehringer discloses a powder inhaler device in which a powder cavity is provided with an air outlet opening into the lower surface of an air flow path which narrows in the region of the outlet opening. The cavity also has an air inlet which does not open into the flow path. A venturi is created by the narrowing flow path adjacent the outlet, giving rise to low pressure in this area when flow is generated by a user inhaling. Air is thereby drawn through the cavity from the inlet to the outlet and then into the flow path.

In spite of the numerous prior art devices there is a need for a device which is simple in design and therefore inexpensive, compact in size and also simple to operate, but which also allows for efficient emptying of a cavity of powder. Consistent and efficient emptying is important to avoid wastage of expensive medicament by leaving it in the device and to avoid residual powder contaminating the device and being inadvertently inhaled on subsequent uses of the device.

There is also a need for a device which efficiently deaggregates powder before being administered. It is desirable for the deaggregation process to result in a significant proportion of the powder particles being in a certain aerodynamic size range. This is often referred to as classifying the powder particles. Various ways of enabling deaggregation are described in the prior art. For example, tortuous flow paths can cause deaggregation as particles impact the walls of the flow path. Alternatively, obstructions can be placed in the flow path downstream of the powder cavity or reservoir. Vibrating or shaking is another possibility. U.S. Pat. No. 4,446,862, discussed above, provides for the capsule to be moved rapidly on inhalation to loosen the powder contents and thereby aid deaggregation of highly cohesive or compacted powders.

Devices employing deaggregation features in the downstream flow passage may become clogged or contaminated in use, since medicament powder may accumulate on these downstream features. It is of course desirable to reduce or avoid the risk of administering an inaccurate amount of medicament powder. Where powder accumulates on downstream deaggregation features, a risk is that accumulated powder from several doses may dislodge suddenly from these downstream features (e.g. if the device is dropped) resulting in the patient receiving a significant over-dose. Accordingly, there is a need to mitigate or eliminate downstream powder accumulation.

SUMMARY

We have discovered that the phenomenon of shear-driven cavity flow may be employed to produce a compact and simple device for efficiently entraining and deaggregating medicament powder.

A trend in dry powder inhaler devices is to have shallow cavities into which flow is directed in order to entrain particles and empty the cavity efficiently. Especially for larger doses of powder, the use of shallow cavities can result in devices which are relatively large, since such a cavity may occupy a relatively large area. We have found, however, that a relatively deep cavity may be emptied very efficiently by designing the device so as to take advantage of the phenomenon of shear driven cavity flow in the powder cavity.

The concept of shear driven cavity flow as known in the field of fluid dynamics is that a rotating flow in a cavity may result from passing a fluid stream across the opening of the cavity (distinct from directing flow into the cavity or using an airflow to create low pressure by the venturi effect above an opening of the cavity to draw a fluid stream through it). The flow tends to rotate in a cylindrical pattern.

It is somewhat counter-intuitive that generating a cylindrical rotating flow in a powder-containing cavity may result in fast and effective emptying of the cavity, rather than simply causing powder to be entrained in the rotating flow. However, we have found that powder may be quickly transferred from the rotating flow to the linear flow over the cavity, rather than remaining for a long period entrained in the rotating flow.

We have found that the shear driven cavity flow effect, preferably in a relatively deep cavity, may be enhanced by manipulating one or more parameters such as flow path design, cavity shape, pressure drop, flow velocity or volume flow rate. We have found that not only fast cavity emptying but also deaggregation or classifying of powder in the cavity can be achieved very effectively in a deep cavity by employing the shear driven cavity flow phenomenon.

One aspect of the invention features a dry powder inhaler device for dispensing an air stream carrying a dose of medicament powder. The inhaler device defines a flow passage and a powder storage cavity having a cavity opening. The cavity opening is disposed in a wall of the flow passage and the flow passage is arranged to direct a flow of air across the cavity opening. The cavity opening has a length in the flow direction and has a depth. The cavity opening length is (i) between 50% and 150% of the cavity depth, and (ii) at least 80% of a maximum length of the cavity in the flow direction. The flow passage has a maximum height immediately adjacent the cavity. The maximum height is between 0.5 mm and 4 mm.

The flow passage can be contoured to avoid directing flow into the cavity. For example, the cavity opening can be formed in a flat wall of the flow passage with a parallel wall opposite the cavity opening. In some embodiments, the geometry and dimensions may generate airflow of the correct characteristics to result in efficient emptying and deaggregation of powder contained in the cavity. In some embodiments, the maximum height of the flow passage adjacent the cavity can be between 0.5 mm and 3 mm, more preferably between 1 mm and 2 mm. The flow passage can be arranged to create a substantially unidirectional flow across the cavity opening. This would be in contrast, for example, to the flow across the cavity described in U.S. Pat. No. 4,446,862 which is (in plan view) fan shaped: although this flow has an overall direction which could be said to be along the line of symmetry of the fan shape, it could not be described as "unidirectional". Furthermore, the height of the flow passage adjacent the cavity in U.S. Pat. No. 4,446,862, being 10 mm or more, may allow for substantial vertical deviations in the flow.

The maximum width (see definition below) of the flow passage in the region of the cavity can be between 2 mm and 6 mm. The cross sectional area of the passage adjacent the cavity may therefore be in the range 1 $mm^2$ to 20 $mm^2$, preferably 3 $mm^2$ to 10 $mm^2$.

The cavity opening can be generally of quadrilateral shape, such as rectangular or trapezoidal. The fillet radii may be 0.001 mm to 0.5 mm, preferably 0.01 mm to 0.3 mm. In some embodiments, a cavity opening of this shape may promote the cylindrical flow pattern characteristic of shear driven cavity flow more effectively than, say, a circular opening. The opening can have an aspect ratio in the range 1.5 to 4.0, more preferably 1.8 to 3.5, still more preferably 2.6 to 3.2. The larger dimension can be aligned with the direction of flow in the flow passage.

The length of the cavity opening in the flow direction can be between 75% and 140% of the cavity depth, more preferably between 90% and 135%. In some embodiments, this may promote shear driven flow in the cavity.

The geometry of the lower front and/or rear edges of the cavity may be another factor that promotes shear driven cavity flow with respect to the flow direction. The lower front and/or rear edges can have a radius of between 1 mm and 3 mm, preferably between 1.5 mm and 2.5 mm. This is distinct from the fillet radii of the cavity opening and vertical corners/edges of the cavity, as mentioned above.

The cavity itself can have a depth as defined below between 3 mm and 10 mm, preferably between 4 mm and 6 mm. The maximum length in the flow direction can be between 3 mm and 10 mm, preferably between 4 mm and 7 mm. The average width of the cavity can be between 1.5 mm and 5 mm, preferably between 2 mm and 3 mm. As well as defining an appropriate volume for containing medicament powder in a dry powder inhaler, the dimensions may promote effective emptying and deaggregation.

An initial study used a simple cuboid shaped cavity (see e.g. FIG. 1). Physical models of such cavities were constructed, filled with powder and tested, the results being recoded using high speed video techniques. Cavity emptying similar to that shown in FIGS. **3*a* to 3*d*** was observed. In an attempt to improve the performance, the cavity shape was modified to include a large radius (of the order of 2 mm) on the lower upstream edge since this reflected the erosion pattern of the powder during the emptying process. This was found to improve the emptying of the cavity. Further work using computational fluid dynamics techniques (described in more detail below) has resulted in the development of shapes for the cavity which have a large radius on the both the upstream and downstream lower edges of the cavity.

A flow-perturbing member can project from a flow passage wall. The flow perturbing member can be located with its most upstream extent between 1 mm and 20 mm upstream of the cavity, preferably between 2 mm and 10 mm, more preferably between 3 mm and 7 mm. This flow perturbing member or members may increase the turbulence in the flow across the cavity, which in turn may increase the turbulence of the induced rotating flow in the cavity. This may increase the efficiency with which the cavity is emptied of powder.

Work using computational fluid dynamics techniques with different designs of flow-perturbing member has confirmed that a markedly increased performance can be obtained. The exact shape and lateral position of the member may also have an effect.

The flow-perturbing member can project from a wall in which the cavity opening is formed (i.e. from the "floor" of the passage). The member can extend across the full height of the passage or across the full width of the passage. In some embodiments, the member only extends over from 1% to 50%, more preferably from 1% to 20%, of the width and/or height of the passage. The cross sectional area of the member in the direction of the flow can be from 1 to 25% of the cross section of the flow passage (perpendicular to the flow) in the vicinity of the member. In some embodiments, the cross section of the member is from 3 to 20%, more preferably 5 to 15%, of the cross section of the flow passage in the vicinity of the member.

A lid member can be associated with the cavity. The lid can be movable between a first position, in which the cavity is closed, and a second position, in which the cavity is open. The lid member can provide part of the boundary of the flow passage.

In some embodiments, the device can include a second powder storage cavity opening into the flow passage downstream of the first said cavity. This arrangement can be used to administer two separate medicaments in the same inhalation. In some embodiments, a lid member can be used to close or open both cavities as it moves between its first and second positions.

The device can have a plurality of flow passages arranged around the circumference of a circle. The flow passages can be arranged such that the flow direction is radial with respect to the said circle. The device can include at least one said powder storage cavity being associated with each flow passage. In this way, a conveniently shaped multi-dose inhaler may be provided. The cavities can be provided in a disc member, which can be arranged to be rotatable with respect to an inhaler mouthpiece, in order sequentially to bring into registry with the mouthpiece unused powder-containing cavities. In some embodiments, a disc member can include a cavity opening having a trapezium shape with the line of symmetry located along the direction of flow in the flow passage. A trapezium shaped cavity opening in a disc member may help to maximise the number of cavities which can be fitted into a given size of disc.

A multi-dose device can have a radially outward flow direction, with an inlet near the centre of the device and a mouthpiece located at the periphery. For example, if the multi-dose device has cavities with trapezium shaped openings, the direction of flow can be from the smaller to the larger end of the opening. In other embodiments, a multi-dose device can have an inlet at the periphery and a centrally located mouthpiece, in which case the flow across any trapezium shaped cavities can be from the larger to the smaller end.

According to another aspect of the invention, a device for dispensing an air stream carrying a dose of medicament powder defines a flow passage and a powder storage cavity having a cavity opening and a lid member movable between a first position in which the cavity is closed and a second position in which the cavity is open. The lid member provides part of the boundary of a flow passage (e.g., when the lid member is in the second position). The cavity opening is in a wall of the flow passage and the flow passage is arranged to direct a flow of air across the cavity opening. The length of the cavity opening in the flow direction is between 50% and 150% of the cavity depth and the maximum height of the flow passage adjacent the cavity is between 0.5 mm and 4 mm. In some embodiments, the length of the cavity opening in the flow direction is at least 80% of the maximum length of the cavity in the flow direction.

In some embodiments, the device can include a second powder storage cavity opening into the flow passage. For example, the device can be used to administer two separate medicaments in the same inhalation. The second cavity can be closed when a lid member in the first position and open when the lid member is in the second position.

In another aspect, a dry powder inhaler device for dispensing an air stream carrying a dose of medicament powder defines a flow passage and a powder storage cavity having a cavity opening. The cavity opening is in a wall of the flow passage and the flow passage is arranged to direct a flow of air across the cavity opening. The length of the cavity opening in the flow direction is (i) between 50% and 150% of the cavity depth, and (ii) at least 80% of the maximum length of the cavity in the flow direction. The flow passage adjacent the cavity has a cross sectional area in the range 1 mm$^2$ to 15 mm$^2$. In some embodiments, the flow passage adjacent the cavity has a cross sectional area in the range 3 mm$^2$ to 10 mm$^2$.

In an inhaler for use by human patients, the total pressure drop across the device in use can be between 2 kPa and 6 kPa. The pressure difference in the flow passage from one end of the cavity to the other can be from 0.1 kPa to 5 kPa, preferably 0.5 kPa to 2 kPa. The flow passage dimensions referred to above may result in a pressure drop in this range for an inhaler designed for use by a human patient.

According to another aspect of the invention, a dry powder inhaler device for dispensing an air stream carrying a dose of medicament powder defines a flow passage and a powder storage cavity having only a single opening The cavity opening is in a wall of the flow passage and the flow passage is arranged to direct a flow of air across the cavity opening. The length of the cavity opening in the flow direction is between 50% and 150% of the cavity depth. The maximum height of the flow passage immediately adjacent the cavity is between 0.5 mm and 4 mm.

According to another aspect, a dry powder inhaler device for dispensing an air stream carrying a dose of medicament powder defines a flow passage and a powder storage cavity having only a single opening. The cavity opening is in a wall of the flow passage and the flow passage is arranged to direct a flow of air across the cavity opening. The length of the cavity opening in the flow direction is between 50% and 150% of the cavity depth. The flow passage adjacent the cavity has a cross sectional area in the range 1 mm$^2$ to 15 mm$^2$. In some embodiments, the flow passage adjacent the cavity has a cross sectional area in the range 3 mm$^2$ to 10 mm$^2$.

The device can be loaded with a dosage form including a compound or combination selected from the list which appears below.

The shape of the cavity may have an important effect on the performance. Because the shear driven cavity flow phenomenon tends to produce a cylindrical rotating flow pattern, a cavity of generally rectangular or trapezoidal shape in plan view, at least for some of its depth, e.g. at least the upper half of the cavity (the half nearer the opening, based on the perpendicular distance from the cavity opening to the furthest extent of the cavity), may promote a rotating cavity flow. By plan view it is meant the view looking at the cavity in a direction normal to the plane of the cavity opening (as defined). The longitudinal line of symmetry of the rectangular or trapezoidal opening preferably is oriented in the direction of the airflow in the flow passage.

In order to generate shear driven cavity flow, the opening of the cavity should may have a cross sectional area which is of the same order as the maximum cross section of the cavity in a plane parallel to the cavity opening, e.g. at least 80% of the maximum cross section, preferably at least 90%, more preferably about 100%.

The cavity is provided with a headspace between the powder fill level (when the powder surface is level and parallel with the cavity opening) and the cavity opening; the headspace can be from 1 mm to 6 mm.

Another aspect of the invention features a replacement magazine configured to be received in a device as described in any of the preceding paragraphs. The replacement magazine includes a cavity or cavities charged with medicament powder for use in a device as described in any of the preceding paragraphs.

Another aspect of the invention features a cavity disc for a dry powder inhaler, the cavity disc defining a plurality of powder-containing cavities arranged in a circular pattern on the disc. The cavity disc is shaped generally as a solid disc or as an annulus. The cavities each have a trapezoid-shaped opening. Each cavity has a radial direction length that is from 50% to 150% of a depth of the cavity. The openings can be covered by a removable seal or lid.

In some embodiments, the length in a radial direction of each cavity can be at least 80% of the maximum length of the cavity in the said radial direction.

In some embodiments, the lower front and/or rear edges of the cavity (33), with respect to the flow direction, can have a radius of between 0.5 and 3 mm, preferably between 1.5 mm and 2.5 mm, more preferably between 1.75 mm and 2.25 mm.

A device as described in any of the preceding paragraphs can be charged with medicament powder in the cavity or cavities.

The medicament powder can contain various active ingredients. The active ingredient can be selected from any therapeutic or diagnostic agent. For example, the active ingredient can be an antiallergic, a bronchodilator (e.g. a beta2-adrenoceptor agonist or a muscarinic antagonist), a bronchoconstrictor, a pulmonary lung surfactant, an analgesic, an antibiotic, a mast cell inhibitor, an antihistamine, an antiinflammatory, an antineoplastic, an anaesthetic, an antitubercular, an imaging agent, a cardiovascular agent, an enzyme, a steroid, genetic material, a viral vector, an antisense agent, a protein, a peptide, a non-steroidal glucocorticoid Receptor (GR Receptor) agonist, an antioxidant, a chemokine antagonist (e.g. a CCR1 antagonist), a corticosteroid, a CRTh2 antagonist, a DP1 antagonist, an Histone Deacetylase Inducer, an IKK2 inhibitor, a COX inhibitor, a lipoxygenase inhibitor, a leukotriene receptor antagonist, an MPO inhibitor, a p38 inhibitor, a PDE inhibitor, a PPARγ agonist, a protease inhibitor, a statin, a thromboxane antagonist, a vasodilator, an ENAC blocker (Epithelial Sodium-channel blocker) and combinations thereof.

Examples of specific active ingredients that can be incorporated in the medicament powder include:

(i) antioxidants: Allopurinol, Erdosteine, Mannitol, N-acetyl cysteine choline ester, N-acetyl cysteine ethyl ester, N-Acetylcysteine, N-Acetylcysteine amide and Niacin;

(ii) chemokine antagonists: BX471 ((2R)-1-[[2-[(aminocarbonyl)amino]-4-chlorophenoxy]acetyl]-4-[(4-fluorophenyl)methyl]-2-methylpiperazine monohydrochloride), CCX634, N-{2-[((2S)-3-{[1-(4-chlorobenzyl)piperidin-4-yl]amino}-2-hydroxy-2-methylpropyl)oxy]-4-hydroxyphenyl}acetamide (see WO 2003/051839), and 2-{2-Chloro-5-{[(2S)-3-(5-chloro-1'H,3H-spiro[1-benzofuran-2,4'-piperidin]-1'-yl)-2-hydroxypropyl]oxy}-4-[(methylamino)carbonyl]phenoxy}-2-methylpropanoic acid (see WO 2008/010765), 656933 (N-(2-bromophenyl)-N'-(4-cyano-1H-1,2,3-benzotriazol-7-yl)urea), 766994 (4-({[({[(2R)- 4-(3,4-dichlorobenzyl)morpholin-2-yl]methyl}amino)carbonyl]-amino}methyl)benzamide), CCX-282, CCX-915, Cyanovirin N, E-921, INCB-003284, INCB-9471, Maraviroc, MLN-3701, MLN-3897, T-487 (N-{1-[3-(4-ethoxyphenyl)-4-oxo-3,4-dihydropyrido[2,3-d]pyrimidin-2-yl]ethyl}-N-(pyridin-3-ylmethyl)-2-[4-(trifluoromethoxy)phenyl]acetamide) and Vicriviroc (iii) Corticosteroids: Alclometasone dipropionate, Amelometasone, Beclomethasone dipropionate, Budesonide, Butixocort propionate, Ciclesonide, Clobetasol propionate, Desisobutyrylciclesonide, Etiprednol dicloacetate, Fluocinolone acetonide, Fluticasone Furoate, Fluticasone propionate, Loteprednol etabonate (topical) and Mometasone furoate.

(iv) DP1 antagonisits: L888839 and MK0525;

(v) Histone deacetylase inducers: ADC4022, Aminophylline, a Methylxanthine or Theophylline;

(vi) IKK2 inhibitors: 2-{[2-(2-Methylamino-pyrimidin-4-yl)-1H-indole-5-carbonyl]-amino}-3-(phenyl-pyridin-2-yl-amino)-propionic acid;

(vii) COX inhibitors: Celecoxib, Diclofenac sodium, Etodolac, Ibuprofen, Indomethacin, Meloxicam, Nimesulide, OC1768, OC2125, OC2184, OC499, OCD9101, Parecoxib sodium, Piceatannol, Piroxicam, Rofecoxib and Valdecoxib;

(viii) Lipoxygenase inhibitors: Ajulemic acid, Darbufelone, Darbufelone mesilate, Dexibuprofen lysine (monohydrate), Etalocib sodium, Licofelone, Linazolast, Lonapalene, Masoprocol, MN-001, Tepoxalin, UCB-35440, Veliflapon, ZD-2138, ZD-4007 and Zileuton ((±)-1-(1-Benzo[b]thien-2-ylethyl)-1-hydroxyurea);

(ix) Leukotriene receptor antagonists: Ablukast, Iralukast (CGP 45715A), Montelukast, Montelukast sodium, Ontazolast, Pranlukast, Pranlukast hydrate (mono Na salt), Verlukast (MK-679) and Zafirlukast;

(x) MPO Inhibitors: Hydroxamic acid derivative (N-(4-chloro-2-methyl-phenyl)-4-phenyl-4-[[(4-propan-2-ylphenyl)sulfonylamino]methyl]piperidine-1-carboxamide), Piceatannol and Resveratrol;

(xi) Beta2-adrenoceptor agonists: metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol, indacaterol, salmeterol (e.g. as xinafoate), bambuterol (e.g. as hydrochloride), carmoterol, indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide; 3-(4-{[6-({(2R)-2-hydroxy-2-[4-hydroxy-3-(hydroxy-methyl)phenyl]ethyl}amino)-hexyl]oxy}butyl)benzene-sulfonamide; GSK 159797, GSK 159802, GSK 597901, GSK 642444, GSK 678007; and a compound selected from N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(3-chlorophenyl)ethoxy]propanamide, 7-[(1R)-2-({2-[(3-{[2-(2-Chlorophenyl)ethyl]amino}propyl)thio]ethyl}amino)-1-hydroxyethyl]-4-hydroxy-1,3-benzothiazol-2(3H)-one, and N-Cyclohexyl-N³-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. wherein the counter ion is hydrochloride (for example a monohydrochloride or a dihydrochloride), hydrobromide (for example a monohydrobromide or a dihydrobromide), fumarate, methanesulphonate, ethanesulphonate, benzenesulphonate, 2,5-dichlorobenzenesulphonate, p-toluenesulphonate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), D-mandelate, L-mandelate, cinnamate or benzoate.)

(xii) Muscarinic antagonists: Aclidinium bromide, Glycopyrrolate (such as R,R-, R,S-, S,R-, or S,S-glycopyrronium bromide), Oxitropium bromide, Pirenzepine, telenzepine, Tiotropium bromide, 3(R)-1-phenethyl-3-(9H-xanthene-9-carbonyloxy)-1-azoniabicyclo[2.2.2] octane bromide, (3R)-3-[(2S)-2-cyclopentyl-2-hydroxy-2-thien-2-ylacetoxy]-1-(2-phenoxyethyl)-1- azoniabicyclo[2.2.2]actane bromide, a quaternary salt (such as [2-((R)-Cyclohexyl-hydroxy-phenyl-methyl)-oxazol-5-ylmethyl]-dimethyl-(3-phenoxy-propyl)-ammonium salt, [2-(4-Chloro-benzyloxy)-ethyl]-[2-((R)-cyclohexyl-hydroxy-phenyl-methyl)-oxazol-5-ylmethyl]-dimethyl-ammonium salt and (R)-1-[2-(4-Fluoro-phenyl)-ethyl]-3-((S)-2-phenyl-2-piperidin-1-yl-propionyloxy)-1-azonia-bicyclo[2.2.2]octane salt wherein the counter-ion is, for example, chloride, bromide, sulfate, methanesulfonate, benzenesulfonate (besylate), toluenesulfonate (tosylate), napthalenebissulfonate (napadisylate or hemi-napadisylate), phosphate, acetate, citrate, lactate, tartrate, mesylate, maleate, fumarate or succinate)

(xiii) p38 Inhibitors: 681323, 856553, AMG548 (2-[[(2S)-2-amino-3-phenylpropyl]amino]-3-methyl-5-(2-naphthalenyl)-6-(4-pyridinyl)-4(3H)-pyrimidinone), Array-797, AZD6703, Doramapimod, KC-706, PH 797804, R1503, SC-80036, SCIO469, 6-chloro-5-[[(2S,5R)-4-[(4-fluorophenyl)methyl]-2,5-domethyl-1-piperazinyl]carbonyl]-N,N,1-trimethyl-α-oxo-1H-indole-3-acetamide, VX702 and VX745 (5-(2,6-dichlorophenyl)-2-(phenylthio)-6H-pyrimido[1,6-b]pyridazin-6-one);

(xiv) PDE Inhibitors: 256066, Arofylline (3-(4-chlorophenyl)-3,7-dihydro-1-propyl-1H-Purine-2,6-dione), AWD 12-281 (N-(3,5-dichloro-4-pyridinyl)-1-[(4-fluorophenyl)methyl]-5-hydroxy-α-oxo-1H-indole-3-acetamide), BAY19-8004 (Bayer), CDC-801 (Calgene), Celgene compound ((βR)-β-(3,4-dimethoxyphenyl)-1,3-dihydro-1-oxo-2H-isoindole-2-propanamide), Cilomilast (cis-4-cyano-4-[3-(cyclopentyloxy)-4-methoxyphenyl]-cyclohexanecarboxylic acid), 2-(3,5-dichloro-4-pyridinyl)-1-(7-methoxyspiro[1,3-benzodioxole-2,1'-cyclopentan]-4-yl)ethanone (CAS number 185406-34-2)), (2-(3,4-difluorophenoxy)-5-fluoro-N-[cis-4-[(2-hydroxy-5-methylbenzoyl)amino]cyclohexyl]-)-3-pyridinecarboxamide), (2-(3,4-difluorophenoxy)-5-fluoro-N-[cis-4-[[2-hydroxy-5-(hydroxymethyl)benzoyl]amino]cyclohexyl]-3-pyridinecarboxamide,), CT2820, GPD-1116, Ibudilast, IC 485, KF 31334, KW-4490, Lirimilast ([2-(2,4-dichlorobenzoyl)-6-[(methylsulfonyl)oxy]-3-benzofuranyl])-urea), (N-cyclopropyl-1,4-dihydro-4-oxo-1-[3-(3-pyridinylethynyl)phenyl]-)-1,8-naphthyridine-3-carboxamide), (N-(3,5-dichloro-4-pyridinyl)-4-(difluoromethoxy)-8-[(methylsulfonyl)amino])-1-dibenzofurancarboxamide), ONO6126, ORG 20241 (4-(3,4-dimethoxyphenyl)-N-hydroxy-)-2-thiazolecarboximidamide), PD189659/PD168787 (Parke-Davis), Pentoxifylline (3,7-dihydro-3,7-dimethyl-1-(5-oxohexyl)-)-1H-purine-2,6-dione), compound (5-fluoro-N-[4-[(2-hydroxy-4-methyl-benzoyl)amino]cyclohexyl]-2-(thian-4-yloxy)pyridine-3-carboxamide), Piclamilast (3-(cyclopentyloxy)-N-(3,5-dichloro-4-pyridinyl)-4-methoxy-benzamide), PLX-369 (WO 2006026754), Roflumilast (3-(cyclopropylmethoxy)-N-(3,5-dichloro-4-pyridinyl)-4-(difluoromethoxy)benzamide), SCH 351591 (N-(3,5-dichloro-1-oxido-4-pyridinyl)-8-methoxy-2-(trifluoromethyl)-5-quinolinecarboxamide), SelCID™ CC-10004 (Calgene), T-440 (Tanabe), Tetomilast (6-[2-(3,4-diethoxyphenyl)-4-thiazolyl]-2-pyridinecarboxylic acid), Tofimilast (9-cyclopentyl-7-ethyl-6,9-dihydro-3-(2-thienyl)-5H-pyrazolo[3,4-c]-1,2,4-triazolo[4,3-a]pyridine), TPI 1100, UCB 101333-3 (N,2-dicyclopropyl-6-(hexahydro-1H-azepin-1-yl)-5-methyl-4-pyrimidinamine), V-11294A (Napp), VM554/VM565 (Vernalis), and Zardaverine (6-[4-(difluoromethoxy)-3-methoxyphenyl]-3(2H)-pyridazinone).

(xv) PDE5 Inhibitors: Gamma-glutamyl[s-(2-iodobenzyl)cysteinyl]glycine, Tadalafil, Vardenafil, sildenafil, 4-phenyl-methylamino-6-chloro-2-(1-imidazolyl)-quinazoline, 4-phenyl-methylamino-6-chloro-2-(3-pyridyl)-quinazoline, 1,3-dimethyl-6-(2-propoxy-5-methanesulphonylamidophenyl)-1,5-dihydropyrazolo[3,4-d]pyrimidin-4-one and 1-cyclopentyl-3-ethyl-6-(3-ethoxy-4-pyridyl)-pyrazolo[3,4-d]pyrimidin-4-one;

(xvi) PPARγ agonists: Pioglitazone, Pioglitazone hydrochloride, Rosiglitazone Maleate, Rosiglitazone Maleate ((−)-enantiomer, free base), Rosiglitazone maleate/Metformin hydrochloride and Tesaglitizar;

(xvii) Protease Inhibitors: Alpha1-antitrypsin proteinase Inhibitor, EPI-HNE4, UT-77, ZD-0892, DPC-333, Sch-709156 and Doxycycline;

(xviii) Statins: Atorvastatin, Lovastatin, Pravastatin, Rosuvastatin and Simvastatin (xix) Thromboxane Antagonists: Ramatroban and Seratrodast;

(xx) Vasodilators: A-306552, Ambrisentan, Avosentan, BMS-248360, BMS-346567, BMS-465149, BMS-509701, Bosentan, BSF-302146 (Ambrisentan), Calcitonin Gene-related Peptide, Daglutril, Darusentan, Fandosentan potassium, Fasudil, Iloprost, KC-12615 (Daglutril), KC-12792 2AB (Daglutril), Liposomal treprostinil, PS-433540, Sitaxsentan sodium, Sodium Ferulate, TBC-11241 (Sitaxsentan), TBC-3214 (N-(2-acetyl-4,6-dimethylphenyl)-3-[[(4-chloro-3-methyl-5-isoxazolyl)amino]sulfonyl]-2-thiophenecarboxamide), TBC-3711, Trapidil, Treprostinil diethanolamine and Treprostinil sodium;

(xxi) ENACs: Amiloride, Benzamil, Triamterene, 552-02, PSA14984, PSA25569, PSA23682 and AER002.

The medicament powder can contain a combination of two or more active ingredients, for example a combination of two or more of the specific active ingredients listed in (i) to (xxi) herein above.

In some embodiments, the medicament powder contains an active ingredient selected from mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propane-sulphonamide, hydrochloride, indacaterol, aclidinium bromide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide); N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate); a [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate); a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate); or a combination of any two or more thereof.

Specific combinations of active ingredients which may be incorporated in the medicament powder include:

(a) formoterol (e.g. as fumarate) and budesonide;

(b) formoterol (e.g. as fumarate) and fluticasone;

(c) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide) and a [2-(4-Chloro-benzyloxy)-ethyl]-[2-((R)-cyclohexyl-hydroxy-phenyl-methyl)-oxazol-5-yl-methyl]-dimethyl-ammonium salt (e.g. hemi-naphthalene-1,5-disulfonate);

(d) N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof (e.g. dihydrobromide) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate);

(e) N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and [2-(4-Chloro-benzyloxy)-ethyl]-[2-((R)-cyclohexyl-hydroxy-phenyl-methyl)-oxazol-5-ylmethyl]-dimethyl-ammonium salt (e.g. hemi-naphthalene-1,5-disulfonate);

(f) N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof (e.g. di-D-mandelate) and a (R)-1-[2-(4-Fluoro-phenyl)-ethyl]-3-((S)-2-phenyl-2-piperidin-1-yl-propionyloxy)-1-azonia-bicyclo[2.2.2]octane salt (e.g. bromide or toluenesulfonate).

In some embodiments, the medicament powder is formulated as an ordered mixture, with fine powder active ingredient particles adhered to larger carrier particles of e.g. lactose.

Another aspect of the invention features a method of dispensing an air stream carrying a dose of medicament powder. The method includes passing a flow of air across the opening of a powder-containing cavity having, the length of the cavity opening in the flow direction being (i) between 50% and 150% of the cavity depth, and (ii) at least 80% of the maximum length of the cavity in the flow direction. The maximum velocity of the flow immediately adjacent the cavity opening is at least 15 m/s. In some embodiments, the maximum velocity of the flow immediately adjacent the cavity opening is at least 20 m/s, more preferably at least 30 m/s, more preferably at least 40 m/s or as much as 50 m/s. In some embodiments, the flow is in the range 15 m/s to 100 m/s, more preferably 20 m/s to 80 m/s.

By generating a flow of this velocity across the opening of the cavity, a rotating flow in the cavity may be created which may give rise to effective emptying and deaggregation. There may, of course, be a variation of flow across the cross section of the passage. The expression "immediately adjacent the cavity opening" includes the plane of the cavity opening as defined below.

In some embodiments, the mass of residual active pharmaceutical ingredient (API) in the cavity after dispensing amounts to between 0.1% and 10% by mass of the total mass of API in the cavity prior to dispensing, preferably between 1% and 8%, more preferably between 1% and 5%. It is normal to measure retention by the mass of API rather than the total powder mass. The term "medicament powder" is used in this specification to mean the complete powder formulation, including API, carrier particles and any other ingredients.

The device is intended to be a platform for delivery of a wide range of powder formulations. Although emptying will vary between different formulations, higher surface shear stress in the lower half of the cavity would normally result in more efficient emptying.

Yet another aspect of the invention features a method of dispensing an air stream carrying a dose of medicament powder includes passing a flow of air across the opening of a powder-containing cavity, the length of the cavity opening in the flow direction being (i) between 50% and 150% of the cavity depth, and (ii) at least 80% of the maximum length of the cavity in the flow direction. The average surface shear stress over the lower half of the cavity is at least 0.5 Pa. In some embodiments, the average surface shear stress over the lower half of the cavity is at least 1 Pa, more preferably at least 1.5 Pa. In some embodiments, the average surface shear stress can be less than or equal to 20 Pa, more preferably less than or equal to 15 Pa. This is based computer modeling of the flow in the cavity, with Reynolds averaged Navier-Stokes (RAND), turbulent, three dimensional, steady computational fluid dynamics (CFD) calculations using the ANSYS® software Fluent, version 6.3.26.

In another aspect, the invention features a method of dispensing an air stream carrying a dose of medicament powder includes passing a flow of air across the opening of a powder-containing cavity having only a single opening. The length of the cavity opening in the flow direction is between 50% and 150% of the cavity depth. The maximum velocity of the flow immediately adjacent the cavity opening is at least 15 m/s. In some embodiments, the flow immediately adjacent the cavity opening is at least 20 m/s, more preferably at least 30 m/s, more preferably at least 40 m/s or as much as 50 m/s. The flow can be in the range 15 m/s to 100 m/s, more preferably 20 m/s to 80 m/s.

Yet another aspect of the invention features a method of dispensing an air stream carrying a dose of medicament powder that includes passing a flow of air across the opening of a powder-containing cavity having only a single opening. The cavity opening has a length in the flow direction of between 50% and 150% of the cavity depth. The average surface shear stress over the lower half of the cavity is at least 0.5 Pa, preferably at least 1 Pa. In some embodiments, the average surface shear stress over the lower half of the cavity is at least 1.5 Pa, the upper end of these ranges being 20 Pa or preferably 15 Pa. This is based on computer modeling of the flow in the cavity, with Reynolds averaged Navier-Stokes (RAND), turbulent, three dimensional, steady computational fluid dynamics (CFD) calculations using the ANSYS® software Fluent, version 6.3.26.

There are also a number of other parameters of the flow in the cavity that are possible to calculate using the computational fluid dynamics technique referred to above. The parameters referred to below are also derived from a computer model with RAND, turbulent, three dimensional, steady CFD calculations using the ANSYS® software Fluent, version 6.3.26.

According to another aspect of the invention, a method of dispensing an air stream carrying a dose of medicament powder includes passing a flow of air across the opening of a powder-containing cavity. The length of the cavity opening in the flow direction being (i) between 50% and 150% of the cavity depth, and (ii) at least 80% of the maximum length of the cavity in the flow direction. The average turbulent kinetic energy in the lower half of the cavity is at least 3 $m^2/s^2$. In some embodiments, the average turbulent kinetic energy in the lower half of the cavity is at least 4 $m^2/s^2$, more preferably at least 5 $m^2/s^2$. In some embodiments, the average turbulent kinetic energy in the lower half of the cavity is less than or equal to 50 $m^2/s^2$, preferably less than or equal to 20 $m^2/s^2$.

According to another aspect of the invention, a method of dispensing an air stream carrying a dose of medicament powder includes passing a flow of air across the opening of a powder-containing cavity. The length of the cavity opening in the flow direction being (i) between 50% and 150% of the cavity depth, and (ii) at least 80% of the maximum length of the cavity in the flow direction. The average vorticity in the lower half of the cavity is at least 2,000 l/s. In some embodiments, the average vorticity in the lower half of the cavity is at least 4,000 l/s, more preferably at least 10,000 l/s. In some embodiments, the average vorticity in the lower half of the cavity is less than or equal to 100,000 l/s, preferably less than or equal to 50,000 l/s, more preferably less than or equal to 20,000 l/s.

According to another aspect, a method for dispensing an air stream carrying a dose of medicament powder includes passing a flow of air across the opening of a powder-containing cavity. The length of the cavity opening in the flow direction is (i) between 50% and 150% of the cavity depth, and (ii) at least 80% of the maximum length of the cavity in the flow direction. The average flow velocity in the lower half of the cavity is at least 1.5 m/s. In some embodiments, the average flow velocity in the lower half of the cavity is at least 3 m/s, more preferably at least 4 m/s. In some embodiments, the average flow velocity in the lower half of the cavity is less than or equal to 30 m/s, preferably less than or equal to 20 m/s, more preferably less than or equal to 10 m/s.

According to another aspect of the invention, a method of dispensing an air stream carrying a dose of medicament powder includes passing a flow of air across the opening of a powder-containing cavity having only a single opening. The cavity opening having length in the flow direction of between 50% and 150% of the cavity depth. The average turbulent kinetic energy in the lower half of the cavity is at least 3 $m^2/s^2$. In some embodiments, the average turbulent kinetic energy in the lower half of the cavity is at least 4 $m^2/s^2$, more preferably at least 5 $m^2/s^2$. In some embodiments, the average turbulent kinetic energy in the lower half of the cavity is less than or equal to 50 $m^2/s^2$, preferably less than or equal to 20 $m^2/s^2$.

According to another aspect of the invention, a method of dispensing an air stream carrying a is dose of medicament powder includes passing a flow of air across the opening of a powder-containing cavity having only a single opening. The cavity opening has a length in the flow direction of between 50% and 150% of the cavity depth. The average vorticity in the lower half of the cavity is at least 2,000 l/s. In some embodiments, the average vorticity in the lower half of the cavity is at least 4,000 l/s, more preferably at least 10,000 l/s. In some embodiments, the average vorticity in the lower half of the cavity is less than or equal to 100,000 l/s, preferably less than or equal to 50,000 l/s, more preferably less than or equal to 20,000 l/s.

According to another aspect of the invention, a method of dispensing an air stream carrying a dose of medicament powder includes passing a flow of air across the opening of a powder-containing cavity having only a single opening. The cavity opening has a length in the flow direction of between 50% and 150% of the cavity depth. The average flow velocity in the lower half of the cavity is at least 1.5 m/s. In some embodiments, the average flow velocity in the lower half of the cavity is at least 3 m/s, more preferably at least 4 m/s. In some embodiments, the average flow velocity in the lower half of the cavity is less than or equal to 30 m/s, preferably less than or equal to 20 m/s, more preferably less than or equal to 10 m/s.

Flow in the cavity as defined in any of the paragraphs above can, in some embodiments, be created solely by the phenomenon of shear driven cavity flow.

In some embodiments, in a method as defined above, the medicament powder includes a compound or combination selected from the list which appears above.

DEFINITIONS

The aspect ratio of the cavity opening is defined as the perpendicular length (in the case of a trapezoidal shape being the length of the line of symmetry) of the opening divided by the mean width.

The term "height", referring to the flow passage shall mean the perpendicular distance from the wall of the passage in which the cavity opening is formed to the opposite wall of the passage.

The term "width", referring to the flow passage, at any given location in the flow passage, shall mean the shortest distance between the two side walls at that location.

The term "floor" shall mean the wall of the flow passage in which the cavity opening is formed.

The term "ceiling" shall mean the wall of the flow passage opposite the floor.

The term "side wall" in relation to the flow passage shall mean a flow passage wall which extends between the floor and the ceiling.

The plane of the cavity opening shall mean the plane defined by the rim of the cavity, the rim being the interface between the cavity and the flow passage. If the rim does not lie completely in one plane, then the plane of the cavity opening shall mean the plane which is the best fit to the rim.

The term "depth" in connection with the cavity shall mean the perpendicular distance from the plane of the cavity opening to the deepest point of the cavity.

The maximum length of the cavity shall be defined as the greatest length of the cavity in the flow direction, measured in a plane parallel to the plane of the cavity opening Where expressions such as "up" and "down" are used with respect to a device in this specification, it is assumed that the orientation of the device is such that the opening of the cavity or cavities faces upwards.

The term "medicament powder" shall mean all of a powder formulation, including without limitation any carrier, diluent or coating in addition to any active pharmaceutical ingredients.

BRIEF DESCRIPTION OF THE DRAWINGS

The present invention will now be described, for exemplary purposes, in more detail by way of embodiments and examples and with reference to the enclosed drawings, in which:

FIGS. 3a-3d are schematic perspective views of part of the flow passage region of FIG. 1, showing a sequence of operation;

FIG. 4 is a plan view of the entire first embodiment;

FIGS. 11a and 11c are side views of computer models of flow paths;

FIGS. 11b and 11d are plan views of the cavities shown in FIGS. 11a and 11c;

EXAMPLE 1

Prior Art

Figure 7:
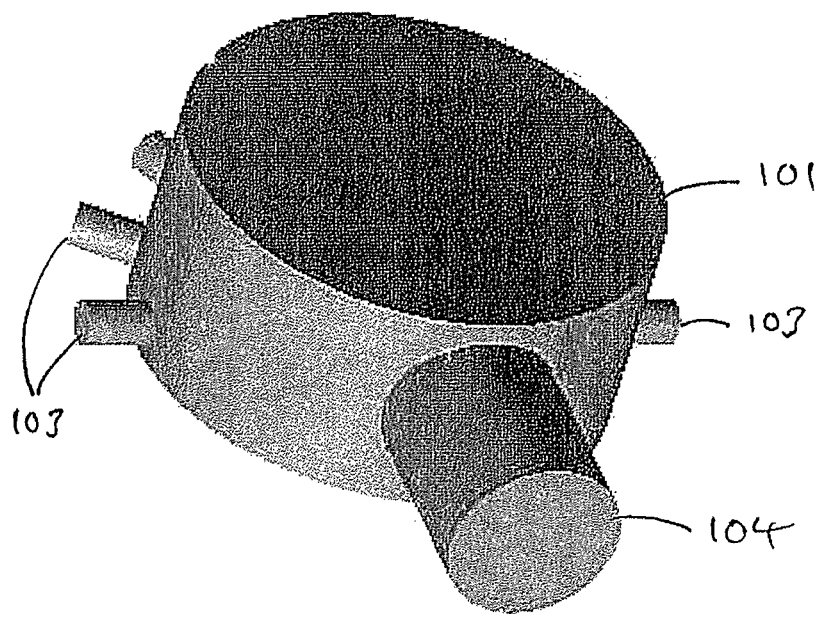
FIG. 7 is a perspective view of a computer model of the flow path of the inhaler of U.S. Pat. No. 4,446,862, used in Example 1.
Figure 8:
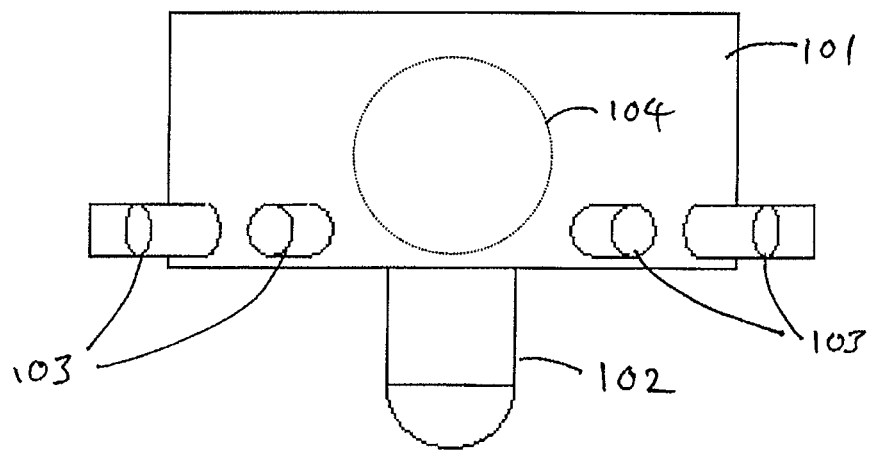
FIG. 8 is a side view of the computer flow path model of FIG. 7.

FIGS. 7 and 8 show a computer model of the flow path of the device described in U.S. Pat. No. 4,446,862 (referred to above). This model is based on the main embodiment described in U.S. Pat. No. 4,446,862, FIGS. 1 to 4a. The device includes a flat cylindrical flow chamber 101, in the base of which is located a separated part 102 of a standard size 4 pharmaceutical capsule containing a powder for inhalation. Evenly spaced around half of the circumference of the chamber and located towards the lower end are six air inlets 103. Symmetrically opposite the inlets 103 is a mouthpiece 104 of rather larger diameter than the inlets 103.

Some dimensions are specified in U.S. Pat. No. 4,446,862. For example the inlet diameter is said to be 2 mm, see col. 6, line 19, and the use of standard size 4 capsules is specified in col. 7, line 15. Size 4 capsules have a capsule base inner diameter of approximately 5 mm and a capsule base length of approximately 7 mm. The remaining dimensions have been taken from FIG. 4a, scaled according to the values which are specified in the text.

The model was used to simulate flow in the device using computational fluid dynamics techniques, specifically Reynolds averaged Navier-Stokes (RANS), turbulent, three-dimensional, steady computational fluid dynamics (CFD) using the ANSYS® software Fluent®, version 6.3.26.

In U.S. Pat. No. 4,446,862, the pressure drop across the device is said to be 4.7 cm H$_2$O (about 0.46 kPa) to produce a flow rate of 28.3 l/min. In the CFD simulation, this pressure drop produced a flow rate of 21.9 l/min, which represents a fairly good correlation of simulated result to the result reported in U.S. Pat. No. 4,446,862. To get a flow rate nearer the target rate according to U.S. Pat. No. 4,446,862, a pressure drop of 0.76 kPa was needed in the model.

The current standard pressure difference for testing inhaler designs is 4 kPa, which is what a normal patient will tend to generate. A weak patient may generate about 2 kPa, whilst a very fit one will generate about 6 kPa.

The table below shows four sets of results for different pressures and corresponding volume flow rates. 4 kPa pressure has been used since it is a modern day standard test condition. 0.46 kPa and 0.76 kPa have been used for reasons discussed above, and 0.17 kPa has been used for reasons which will be explained below in the discussion of Example 2. A number of parameters were computed for each case, labeled 1-8 in Table 1 below, as follows:

Parameter 1: Average shear stress at the cavity surface (Pa) over the whole cavity;

Parameter 2: Average shear stress at the cavity surface (Pa) over lower half of cavity;

Parameter 3: Average flow velocity (ms$^{-1}$) over the whole cavity;

Parameter 4: Average flow velocity (ms$^{-1}$) over lower half of cavity;

Parameter 5: Average vorticity (1/s) over the whole cavity;

Parameter 6 Average vorticity (1/s) over lower half of cavity;

Parameter 7: Average turbulent kinetic energy (m$^2$/s$^2$) over the whole cavity; and Parameter 8: Average turbulent kinetic energy (m$^2$/s$^2$) over lower half of cavity.

The average surface shear stress at the wall of the cavity, for the lower half of the cavity (based on half the perpendicular distance from the plane of the cavity opening to the bottom of the cavity), is considered to represent the best indicator of emptying efficiency for this model. The wall shear stress is defined as:

$$\tau_w = \mu \cdot \frac{\partial v}{\partial n}$$

where

μ is the molecular viscosity and $$\frac{\partial v}{\partial n}$$

the normal velocity gradient at the wall.

In Table 1, ΔP is the pressure difference in kPa and Q is the volume flow rate in l/min.

TABLE 1

| | | PARAMETER | | | | | | | |
|---|---|---|---|---|---|---|---|---|---|
| ΔP (kPa) | Q (l/min) | 1 | 2 | 3 | 4 | 5 | 6 | 7 | 8 |
| 4.00 | 66.53 | 1.72 | 0.43 | 2.73 | 1.18 | 5000 | 1800 | 32.00 | 3.10 |
| 0.46 | 21.90 | 0.28 | 0.06 | 0.39 | 0.85 | 1637 | 592 | 2.49 | 0.26 |
| 0.17 | 12.96 | 0.10 | 0.02 | 0.45 | 0.19 | 876 | 288 | 0.69 | 0.06 |
| 0.76 | 28.58 | 0.45 | 0.08 | 1.11 | 0.49 | 2133 | 724 | 4.70 | 0.45 |

EXAMPLE 2

CFD Modeling of Devices

A computer model of a device designed as an example of one embodying our concepts was created using the same software that was used in Example 1. The entire inhaler device has more automated functions. There are also two flow paths in the inhaler, one which passes over the powder cavity and a bypass passage. The flow path which passes over the cavity is slightly more tortuous than that of the prior art and there may be a moderately significant pressure drop before the flow passage reaches the cavity. For example, there may be a pressure drop in normal use of between 0.01 and 2.0 kPa over the portion of the total flow path leading up to the cavity. This is preferably at the lower end of that range, e.g. 0.1 to 1.0 kPa.

For these reasons, a straight comparison based on overall pressures and volume flows, etc, between the two inhalers is not really the best test. Nonetheless, the whole inhaler was analyzed at 4 kPa pressure difference between air inlet and mouthpiece, with the results shown in row 1 of Table 2 below. The remaining results in Table 2 are for a section of the flow path which corresponds better with the very simple flow path of the device described in U.S. Pat. No. 4,446,862.

Figure 9:
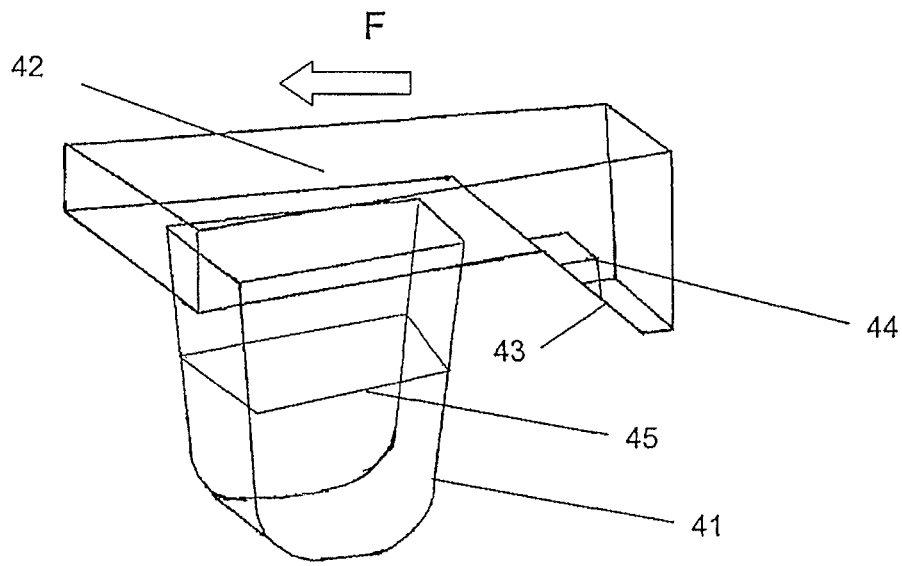
FIG. 9 is a perspective view of a computer model of the flow path of an inhaler, used in Example 2.

The modeled flow path is shown in FIG. 9. This path accurately represents the critical part of the flow as regards emptying of the powder cavity. The cavity is shown at 41 and the flow passage over the cavity at 42. The dimensions of the cavity are given in Table 3 below under column "A". The flow passage adjacent the cavity has height 1.5 mm and the width is 3.1 mm at the upstream end and 5.1 mm at the downstream end, with respect to the flow direction F. Part 43 of the floor of the flow passage 42 on the upstream side of the cavity is sloping. Projecting from this floor is a turbulence-inducing obstruction or projection 44—a so-called "turbulator". The purpose of this feature is to promote turbulence in the flow in the passage 42 which is then imparted to the shear driven flow in the cavity 41. In this example, results were obtained both with and without a turbulator 44 in the flow path; this is indicated in the Table.

The same eight parameters used in Example 1 were computed for the device and the numbered columns in Table 2 below correspond to those of Table 1.

Four of the eight results are parameters average over the whole cavity, whilst the other four are averaged over only the lower half of the cavity. The line 45 half way down the cavity in FIG. 9 shows the division between the upper and lower halves of the cavity: it is located at half the perpendicular distance from the plane of the cavity opening to the bottom of the cavity.

The first row of results is for a standard pressure drop of 4 kPa over a computer model of the to entire inhaler. Approximately 1 kPa of this pressure drop was "lost" over other parts of the inhaler model. For the first row results, therefore, the pressure drop across the flow path shown in FIG. 9 may be assumed to be approximately 3 kPa. The model used for the row 1 results includes a bypass passage, which means that the volume flow rate is very high in comparison with the other results which are for the short section of flow path shown in FIG. 9. The volume flow rate through the FIG. 9 flow passage only is shown in brackets.

The remaining results are for a given pressure drop across only the flow path of FIG. 9. This section of flow path was chosen to be as fair a comparison to the U.S. Pat. No. 4,446,862 device as possible. In three of these cases, the turbulator is included in the flow path. In one case, the turbulator was omitted.

TABLE 2

|  | ΔP (kPa) | Q (l/min) | PARAMETER |  |  |  |  |  |  |  |
|---|---|---|---|---|---|---|---|---|---|---|
|  |  |  | 1 | 2 | 3 | 4 | 5 | 6 | 7 | 8 |
| Whole inhaler - no turbulator | 4.00 | 57.50 (12.1) | 3.46 | 2.00 | 5.14 | 4.44 | 15800 | 10400 | 9.67 | 5.96 |
| With turbulator | 1.50 | 12.26 | 4.17 | 1.87 | 5.38 | 4.36 | 17661 | 11012 | 10.23 | 5.19 |
| Without turbulator | 1.50 | 12.86 | 3.57 | 1.65 | 4.73 | 3.98 | 15563 | 10498 | 8.05 | 4.58 |
| With turbulator | 0.46 | 6.16 | 1.26 | 0.37 | 2.43 | 1.63 | 8108 | 4106 | 3.08 | 1.11 |
| With turbulator | 7.00 | 29.70 | 19.77 | 14.10 | 15.51 | 15.09 | 49053 | 39056 | 45.96 | 32.49 |

In Table 1, ΔP is the pressure difference in kPa and Q is the volume flow rate in l/min.

Comparing the results, it is immediately apparent that a much more energetic flow is induced in the cavity in the device according to this disclosure than in the cavity of U.S. Pat. No. 4,446,862. In line four of Tables 1 & 2, the 0.46 kPa pressure drop specified in U.S. Pat. No. 4,446,862 is applied. The average surface shear stress (Parameter 2) in the lower half of the cavity is 0.37 Pa in the device according to this disclosure and only 0.06 Pa in the device according to U.S. Pat. No. 4,446,862. This difference is more than a factor of 6 in a parameter which, as discussed above, is considered to be the best indicator of cavity emptying efficiency.

Comparing row 1 of the respective tables, where in each case a pressure drop of 4 kPa was applied across the whole inhaler, the values of Parameter 2 are 3.46 Pa and 1.72 Pa, respectively, for the inhaler of this disclosure and the device according to U.S. Pat. No. 4,446,862—a factor of more than 2, despite the fact that pressure losses would have occurred in other parts of the inhaler, and much of the flow would have been through the bypass channel.

In row 3 of Table 2, a pressure drop of 1.5 kPa is applied across the flow path without the turbulator feature; this results in a flow rate of about 12.9 l/min and an average surface shear stress in the lower half of the cavity of 3.57 Pa. A similar flow rate in the device of U.S. Pat. No. 4,446,862 produces an average surface shear stress in the lower half of the cavity of a mere 0.02 Pa.

EXAMPLE 3

A different CFD modeling technique, RANS turbulent, three-dimensional, transient multiphase CFD using the ANSYS® software CFX®, release 11.0, was employed to model the movement of powder in the airflow in the cavities, specifically to obtain results relating to the emptying of the cavities. The software simulated inter-phase momentum transfer using a dispersed particle model with a particle size of 50 micron.

The flow path of Example 2/FIG. 9, without turbulator, was compared to the flow path of Example 1 (the CFD model of the device of U.S. Pat. No. 4,446,862). The same flow rate of 12 l/min was applied to each flow path and, in the model, the cavity was initially filled with powder to ⅔ of the total cavity volume.

Figure 10:
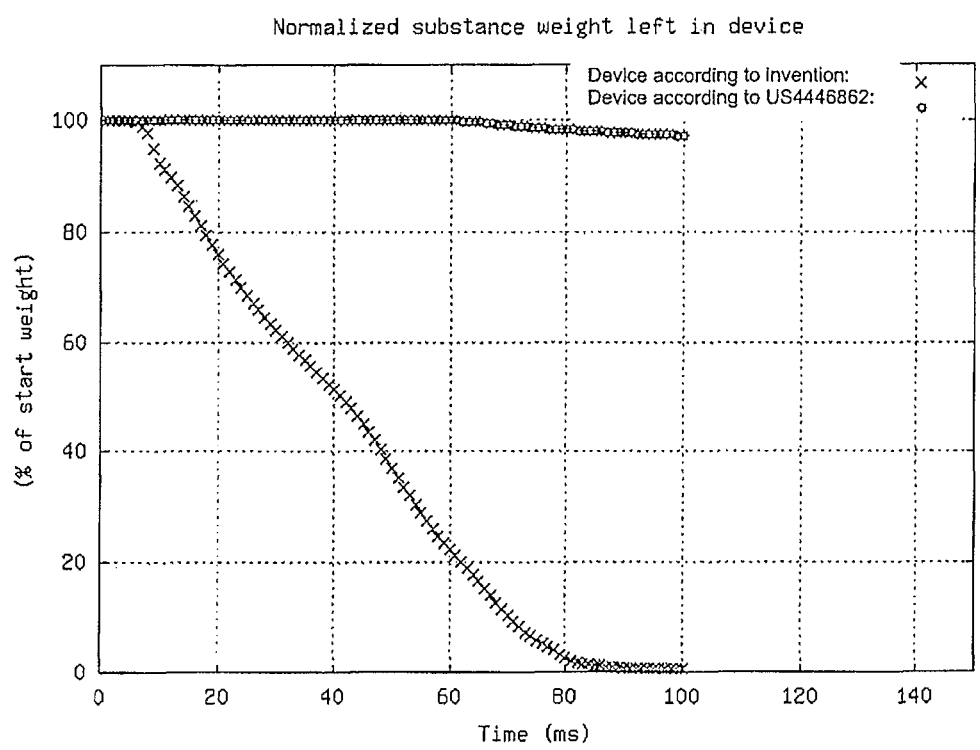
FIG. 10 is a graph showing the results of computer modeling of powder entrainment in the flow path of FIGS. 7 and 8 and also in a flow path.

The simulation was made for the first 100 mS after initiation of airflow. As can be seen from the graph of the results in FIG. 10, after 100 mS, the cavity in the flow path according to this disclosure was substantially empty, whilst the cavity of the U.S. Pat. No. 4,446,862 device still contained more than 90% of the original mass of powder. More powder may subsequently have been entrained in the air flow in the U.S. Pat. No. 4,446,862 device if the simulation had been is extended, but this Example demonstrates at least that the rate of emptying of a cavity in a device or flow path according to this disclosure appears to be markedly superior to that of U.S. Pat. No. 4,446,862. It is generally considered desirable in the inhaler art to entrain powder in as short a time period as possible.

EXAMPLE 4

Referring to FIGS. 11a and 11b, a flow path in accordance with this disclosure is shown. Various dimensions of the cavity were altered in the CFD model referred to in Example 2. These dimensions are shown in FIGS. 11a and 11b and also in Table 3 below. Fillet radius is shown at 207 in FIG. 11b, Rear radius at 203 in FIG. 11a, Front (downstream) radius at 204, Length at 201 and depth at 202. Rear half-width is shown at 205 in FIG. 11b and Front half-width at 206. The flow passage passing over the cavity is shown at 210 and cavity at 211. The direction of flow is indicated by arrow F. One alternative shape of cavity, with corresponding reference numerals indicating equivalent features of the geometry, is shown in FIGS. 11c and 11d. Six designs were tested in total.

Analysis was performed using the same software as in Examples 1 and 2. The model included a turbulator (reference 212 in FIG. 11a). For each geometry, the average surface shear stress over the lower half of the cavity was computed. The results are shown in Table 3 below.

cuboid shape of approximately equivalent overall proportions (length, depth, width). However, the CFD results shown in Table 3 unexpectedly show that considerably better performance is possible by refining the geometry further.

Changing Design A to increase the aspect ratio in plan view—that is to say increasing the length relative to the width—appeared to result in substantially greater surface shear stress in the lower half of the cavity. Furthermore, increasing the size of the front radius (that is to say, the downstream radius) appeared to have a marked effect. These changes can be seen, for example, in Design B which is shown in FIGS. 11c and 11d. For example, the both front and rear radii can be between 1.75 mm and 2.25 mm.

EXAMPLE 5

Physical prototypes of Designs A, B C and F in Example 4 were created using rapid prototyping techniques. These models were then tested using by filling them with two different powder formulations, one very challenging and the other less so. A pressure of 1.5 kPa was applied to each design to generate airflow through the prototypes equivalent to a very weak human patient inhaling. Figures for emptying expressed as the percentage mass of active pharmaceutical ingredient (API) remaining the cavity were determined for each design.

Figure 12:
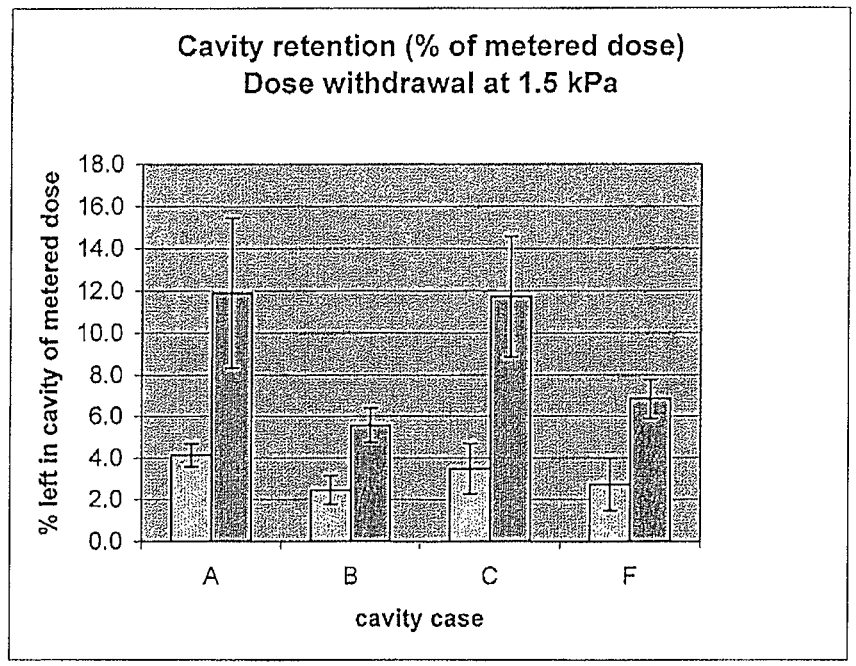
FIG. 12 is a bar chart showing powder retention for four different shapes of cavity.

The results are shown in FIG. 12. The shaded columns represent results for the more challenging formulation, whilst the plain columns represent the less challenging formulation. A marked reduction in retention of API powder can be seen between Design A and Design B, consistent with the CFD results in Table 3. However, an increase in retention is seen from Design B to Design C, despite the fact that the average surface shear stress value in the CFD work for Design C was higher than for Design B. Design F showed retention broadly similar to Design B, although the surface shear stress from the CFD work was higher. It is believed that the main reason for the increased retention of Designs C and F, particularly for Design C, compared with Design B, related more to issue with the manufacturing of the prototypes than with the overall design. It is believed, however, that if properly manufactured and filled, Designs C to F would have lower powder retention

TABLE 3

| Cavity design | A | B | C | D | E | F |
|---|---|---|---|---|---|---|
| Fillet Radius [mm] | 0.3 | 0.2 | 0.22 | 0.2 | 0.2 | 0.201 |
| Rear Radius (lower upstream edge) [mm] | 2 | 2.2 | 2.09 | 2.16 | 2.14 | 2.17 |
| Front Radius (lower downstream edge) [mm] | 1 | 2.2 | 1.8 | 2.1 | 2.06 | 1.8 |
| Length in flow direction [mm] | 4.5 | 5.5 | 4.95 | 5.43 | 5.5 | 5.19 |
| Depth [mm] | 4.5 | 4.2 | 4.58 | 4.95 | 5.5 | 4.46 |
| Length/depth | 1.00 | 1.31 | 1.08 | 1.10 | 1.00 | 1.16 |
| Rear Half Width [mm] | 0.958 | 0.8 | 1.03 | 1.1 | 1.3 | 1.1 |
| Front Half Width [mm] | 1.35 | 1.1 | 0.7 | 0.67 | 0.65 | 0.72 |
| Area Cavity [mm 2] | 58.3 | 57.6 | 56.9 | 67.1 | 79 | 59 |
| Area Lower Half of Cavity [mm 2] | 30.4 | 29.4 | 28.9 | 34.3 | 40.6 | 30.1 |
| Volume Cavity [mm 3] | 39.13 | 35.3 | 32.8 | 40.5 | 51.4 | 35.5 |
| Shear stress Lower Half of Cavity [Pa] | 2.08 | 3.46 | 4.16 | 4.34 | 4.32 | 4.6 |

It can be seen from the results that changing the cavity shape can have a significant effect on the average shear stress. Design A is shown in FIGS. 11a and 11b. This is also the design shown in FIG. 9. This design had been developed using high speed imaging of powder flow in physical models of cavities—it had been determined that this shape produced considerably better emptying of the cavity than a simple than Design B. These "reverse taper" designs (C to F) may also be useful in an inhaler of a different design.

EXAMPLE 6

Similar testing to that of Example 5 was performed using the prototypes for Designs A and B, using 9 different standard and experimental powder formulations.

Figure 13:
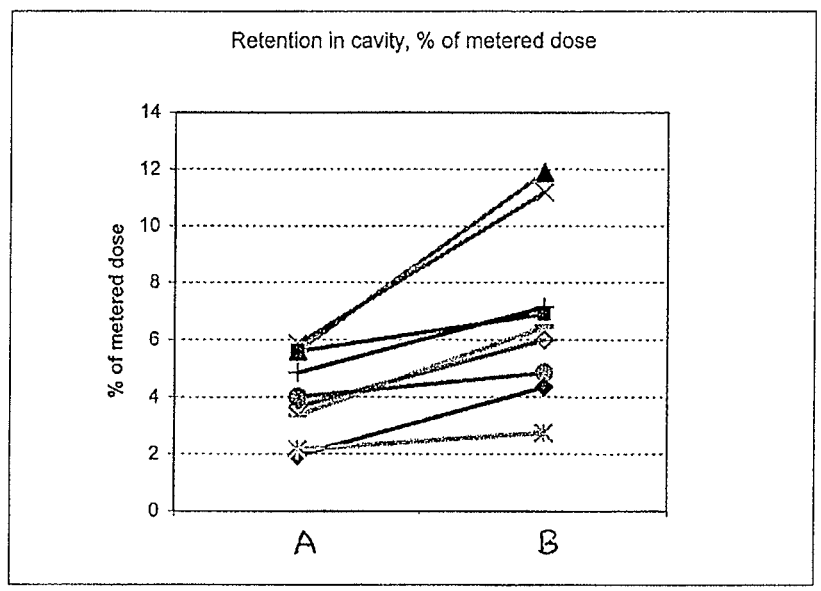
FIG. 13 is a graph showing the degree of powder retention for two alternative designs of cavity and for nine different powder formulations.
Figure 14A:
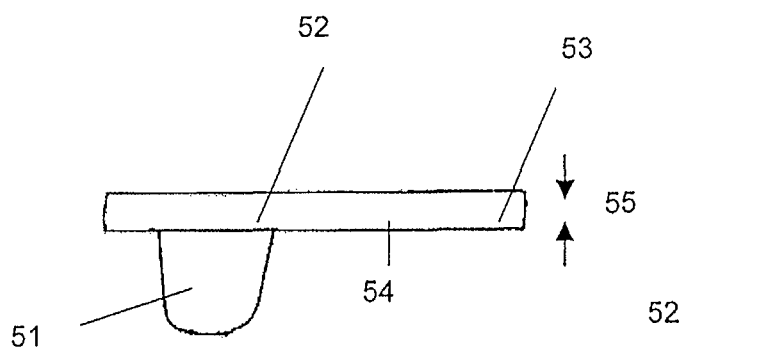
FIGS. 14a and 14b are side and perspective views, respectively, of an alternative flow path model of a device.
Figure 14B:
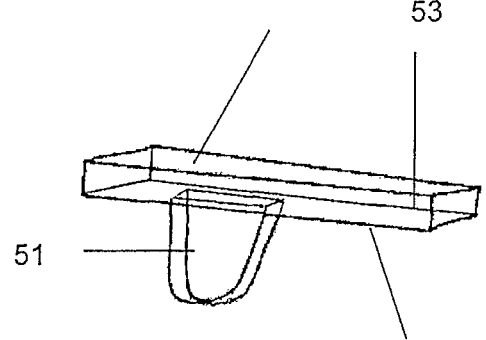
Figure 15A:
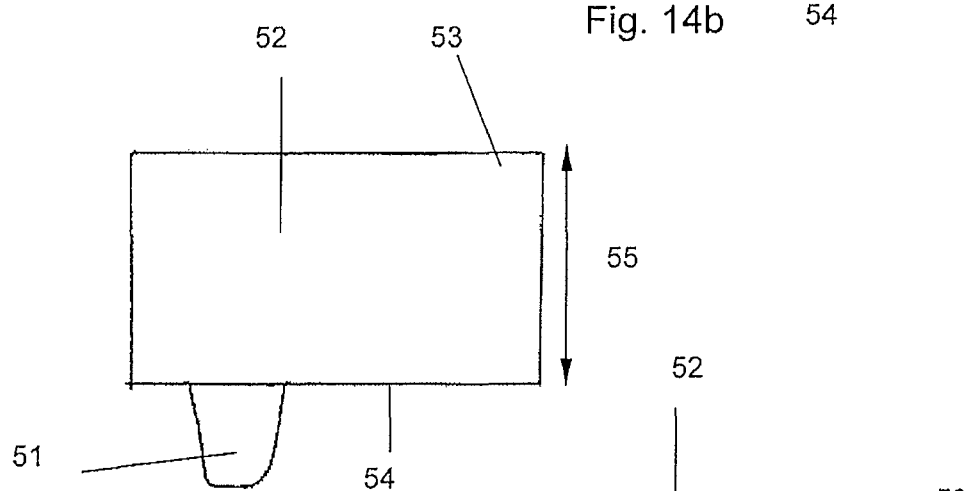
FIGS. 15a and 15b are side and perspective views, respectively, of an alternative flow path model of a device with increases channel height.
Figure 15B:
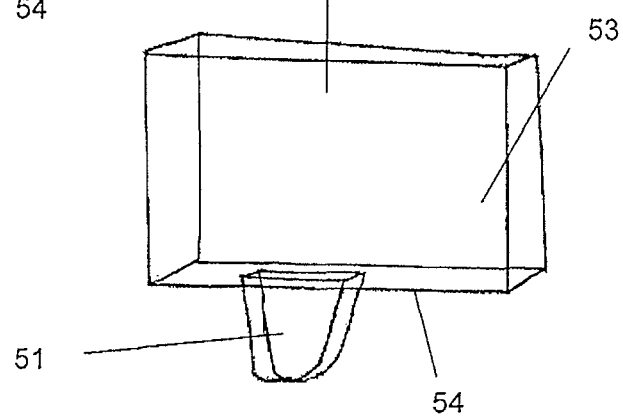

FIG. 13 shows a plot of retention of powder in the cavity for Design A and Design B. As can be seen, for every formulation Design B showed less retention of powder.

For both cavity shapes, the pressure drop across the section of flow path was 1.5 kPa. The average surface shear stress in the lower half of the cavity for the original design (calculated in Example 4) was 2.08 Pa, whilst the same value for the second shape (from Example 4) was 3.46 kPa. This result supports the hypothesis that average surface shear stress in the lower half of the cavity is correlated to emptying efficiency.

EXAMPLE 7

A slightly different computer model of the flow path for a device was generated for the purpose of assessing the effect of flow passage height on the performance of the device. The models for a 1.5 mm channel height and a 10 mm channel height are shown in FIGS. 14a, 14b, 15a, and 15b respectively. The width of the channel was the same for each model, diverging slightly in the downstream direction and being from 3.1 mm at its narrowest to 5.1 mm at its widest point. The upstream part 53 of the flow passage 52 was redesigned to have a flat "floor" 54 (i.e. the wall of the flow path in which the cavity is formed). The reason for this was that it was found that, if the inclined floor was retained, in a model with increased "ceiling" height (i.e. distance 55 from the "floor" to the opposite wall), then the flow was directed upwards and away from the flow passage floor. The inclined upstream passage has relatively little effect when the height of the passage over the cavity is small (e.g. around 1.5 mm), but a fair assessment of the effect of increasing flow passage height could only be made if the passage continued to direct flow across the cavity opening (as opposed to away from it).

A number of different channel heights were modeled, each with a cavity 51 of Design A (see Examples 5 & 6 above).

CFD calculations were made based on a volume flow rate of 25 l/min passing down the channel in each case. The average surface shear stress for the lower half of the cavity was calculated for each case, using the same software as used in Examples 1 and 2, with the same definitions applying. The results are shown in Table 4 below.

TABLE 4

| Flow passage height (mm) | Average surface shear stress - lower half of cavity (Pa) |
|---|---|
| 1.5 | 6.6 |
| 3 | 0.99 |
| 5 | 0.05 |
| 10 | 0.03 |

As can be seen, the result of increasing the flow passage height is a dramatic reduction in the average surface shear stress in the lower half of the cavity. This may be principally due to the reduced airflow velocity across the cavity.

To promote manufacturability and accommodate typical tolerances, the flow passage height is 1.5 mm. However, it is believed that decreasing the flow passage height would further increase the emptying efficiency of the device. Flow passage heights of 1 mm and 0.5 mm are also contemplated.

Interpolating these results, an average surface shear stress value over the lower half of the cavity for a flow passage height of 4 mm would be about 0.5 Pa based on a straight line drawn between the 3 mm and 5 mm values on a graph.

EXAMPLE 8

CFD studies with simple cuboid and capsule shaped cavities were performed and it was found that a cuboid shaped cavity showed more promising results than a capsule shaped cavity. The rate of emptying is found to be slightly slower for a capsule shaped cavity. While the flow in the cuboid shaped cavity is found to be substantially two-dimensional, the flow in the capsule shaped cavity is found to be three-dimensional. The three-dimensional flow in the capsule shaped cavity is found to result in a greater concentration of particles at and near the centerline downstream of the cavity. A major difference is in the capacity to promote a cylindrical flow pattern. It is believed that the capsule-shaped cavity does not allow the build up of a cylindrical flow pattern.

A number of non-limiting embodiments will now be described with reference to FIGS. 1 to 6.

A first embodiment is shown schematically in FIG. 4. This is a multi-dose inhalation device from which a user may inhale doses of medicament in the form of dry powder. The device 1 includes a housing 23 and a mouthpiece 3. The mouthpiece 3 may be uncovered by linear movement of a mouthpiece cover 24. In some embodiments (not shown), the mouthpiece cover can be pivotally supported by the housing.

Inside the housing 23 is a disc-shaped structure 18 containing a plurality of cavities 5. The cavity disc 18 is rotatably supported in a cavity disc holder 19. The cavities 5 are arranged in an annular pattern around the periphery of the disc. The disc 18 has a large central hole 26 which accommodates other components of the inhaler device including an air inlet channel (not shown) and a mechanism (also not shown) for moving the disc around to expose new cavities for each inhalation. A separate flow channel (not shown) is provided over each cavity 5, with the top surface 25 of the disc 18 forming the lower surface of the channel.

FIG. 1 schematically shows a cavity 5 and an adjacent flow path 4 of the first embodiment. The height of the flow path is shown at 13. The cavity 5 is cuboid shaped and the cavity opening 20 has a rim 6 where the sides of the cavity 5 meet the flow passage lower wall or "floor" 7. The cavity contains medicament powder 2. It is advantageous that the cavity is shaped to allow a cylindrical airflow pattern within the cavity 5. The cylindrical flow pattern in the cavity is developed around an axis located transverse to the flow direction and approximately in the middle of the cavity. The sides of the cavity are perpendicular to the floor 7.

Now, with reference to FIGS. 1 and 3 the overall function of the device 1 will be described in more detail. Part of the flow passage 4 has a flat floor 7 (i.e. the lower wall of the passage when the device is in its normal orientation). The floor 7 includes an opening 20 into the powder-containing cavity 5. The passing of an air stream in the flow direction F along the flow passage and across the opening 20 generates a cylindrical circulating flow in the cavity 5 due to the phenomenon of shear driven cavity flow. The powder particles are agitated in this energetic, somewhat turbulent, circulating flow, and also impact the sides of the cavity. The entrainment of particles in the energetic flow and the impacting of particles against the sides of the cavity 5 may contribute to deaggregation, bringing the formulation into a condition ready for inhalation. The powder particles entrained in the circulating flow may tend to be thrown outwardly (or, more precisely, will tend to move tangentially to the flow), and thus may exit the cavity and become entrained in the airflow in the passage 4.

The cavity 5 and cavity opening 20 each have a length 10 in the flow direction F of the flow passage 4 of 5 mm. The cavity depth 22 is also 5 mm.

The distance 11 from the top of the cavity 5 (i.e. the plane of the cavity opening) to the top of the leveled powder particle bed in an initial condition is 1 mm. This distance is referred to as the headspace 11 of the cavity. The depth of powder in the cavity is shown at 9.

In side section, the cavity is square; the inner corners of the cavity are essentially sharp, that is to say the lower front (downstream) edge 16 and the lower rear (upstream) edge 17 are sharp. In some embodiments (not shown), the edges have a radius of about 0.5 mm in order to provide some guidance in the rotational movement of the generated circulating flow.

FIGS. 3a to 3d show schematically the emptying of the cavity 5. Air moves along the passage 4 under the influence of a pressure drop created by a patient inhaling (not shown). For the whole inhaler, this may be between 2 and 6 kPa. The pressure drop over the section of passage shown in FIG. 3 may be between 0.5 kPa and 5 kPa.

FIG. 3a shows the initial state of the powder-filled cavity 5. An airflow along the flow passage 4 is initiated in the flow direction F and emptying of the cavity 5 starts. In FIG. 3b some of the powder 2 has left the cavity 5, the build up of a circulating flow in the cavity 5 has begun and it can be seen that the cavity 5 starts to empty at the downstream end. As can be seen in FIG. 3c, the powder level is gradually eroded downwardly and in an upstream direction. The time elapsed from the initial state in FIG. 3a to the final state in FIG. 3d depends partly speed of the flow and the exact powder composition, but a normal time for this embodiment would be about 300 ms.

Figure 1:
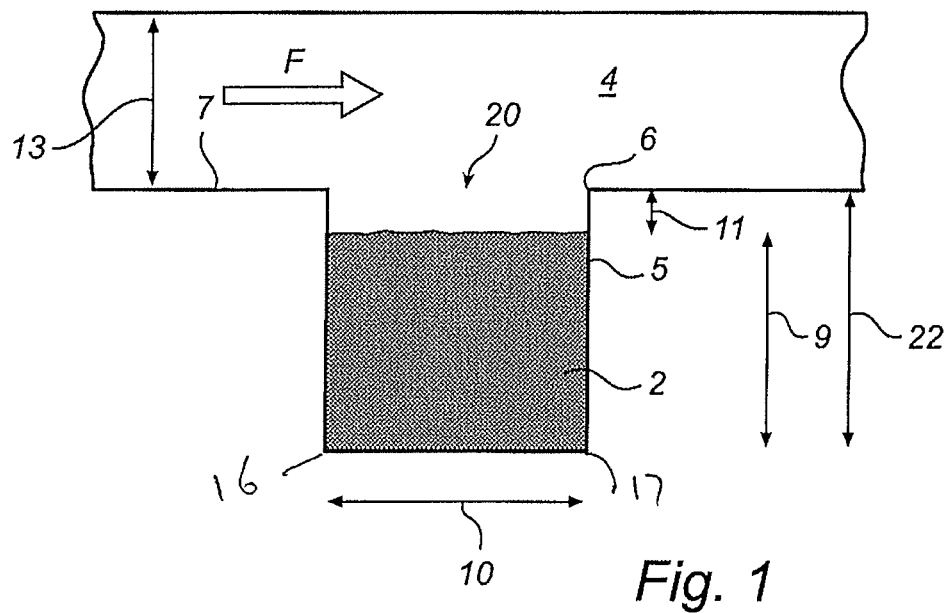
FIG. 1 is a schematic cross sectional view of a flow passage region of a first embodiment.
Figure 2:
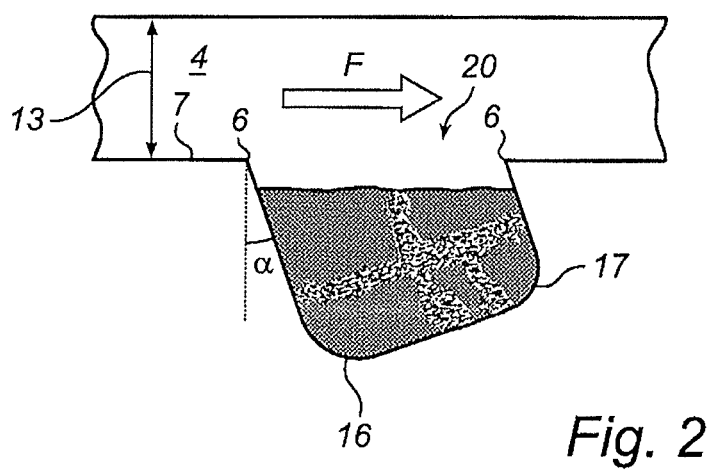
FIG. 2 is a schematic cross sectional view of a flow passage region of a second embodiment.
Figure 5:
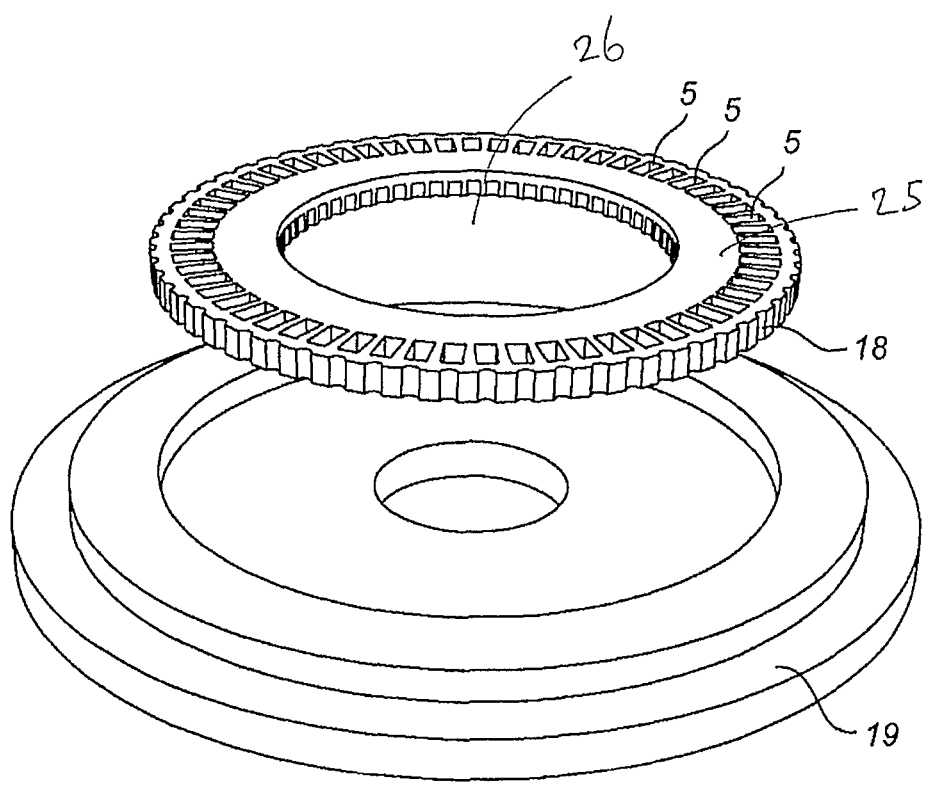
FIG. 5 is an exploded perspective view of a cavity disc and support of the first embodiment.
Figure 6:
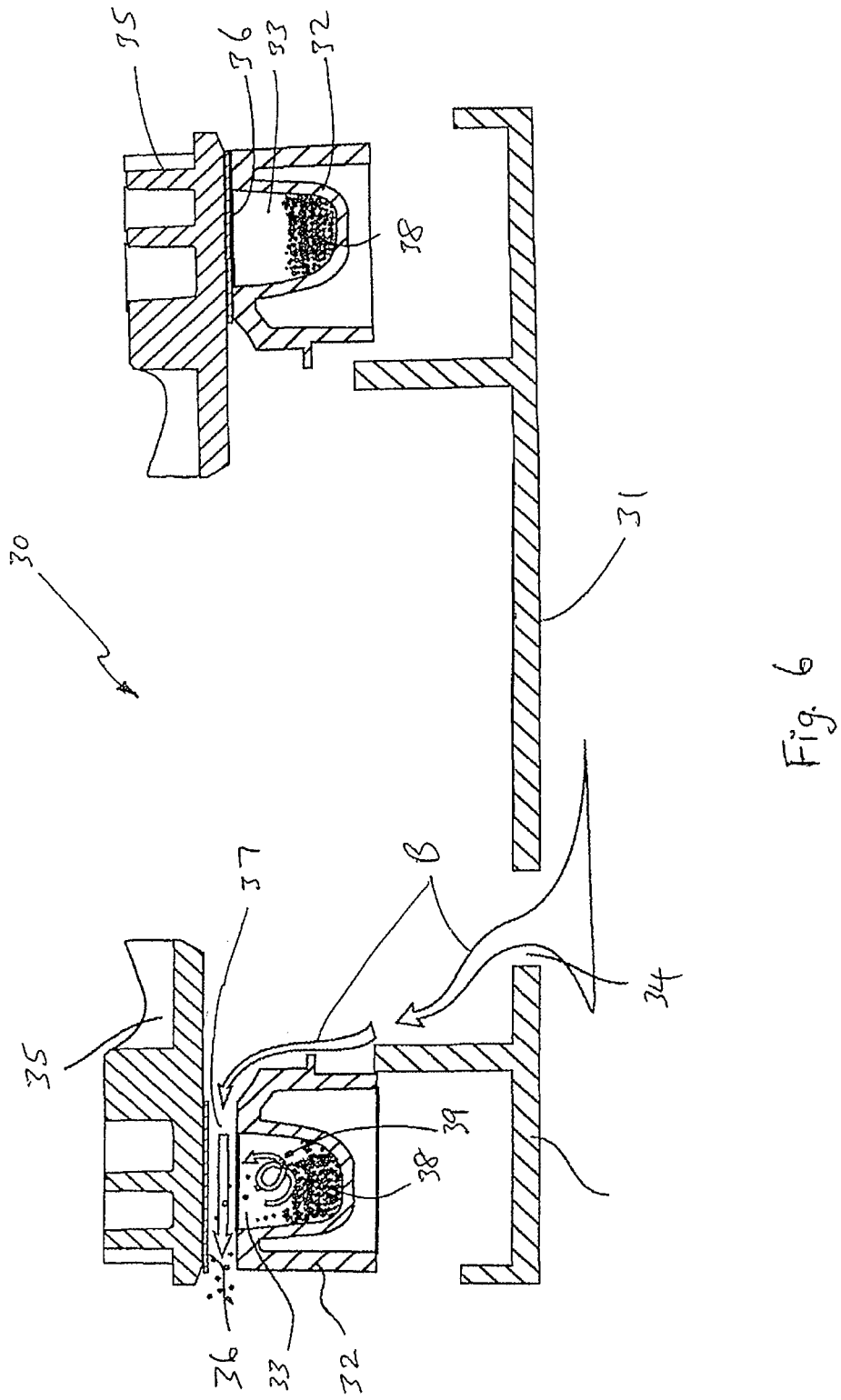
FIG. 6 is a side sectional view of part of a third embodiment, showing the cavity disc and two cavities.

A second embodiment will now be described with reference to FIG. 2. The only aspect which is changed from the first embodiment is the shape of the cavity. Reference numerals in this embodiment are the same as for the first embodiment for equivalent features.

In the second embodiment, the parallel front and rear walls of the cavity 5 are oriented at an acute angle α in relation to the vertical direction (normal to the cavity opening). The cavity opening 20 is still aligned with flow passage floor 7 in the flow passage 4 adjacent the cavity 5. The inclination of the walls in relation to the flow passage 4 may make it more difficult for the particles entrained in the circulating flow in the cavity to escape into the flow passage 4. Hence, in the second embodiment the degree of deaggregation may be increased, since the time for which the medicament powder 2 is entrained in the energetic circulating flow and subject to wall contact/impact is increased. On the other hand, emptying time may be longer for the second embodiment. In FIG. 2 the cavity is shown angled in the direction of flow (arrow F), but in a modification the cavity could be angled in the opposite direction of the cavity shown in FIG. 2, that is to say with the angle α in FIG. 2 having a negative value.

It has been found that powder can be retained by the cavity in the lower upstream and downstream corners/edges. To counteract this, in the second embodiment the lower front (downstream) edge 17 of the cavity 5 has a radius of about 0.5 mm, whilst the lower rear (upstream) edge 16 has a radius of approximately 1 mm.

A third embodiment will now be described with reference to FIG. 6, which shows a part side section through a multi-dose dry powder inhaler 30. A housing member 31, together with other components (not shown) of an inhaler housing, contain the various components of the inhaler.

A cavity disc 32 has a number of powder-containing cavities 33. In use, as with the first embodiment, the disc 32 is rotated in order to bring the individual cavities into registry with a mouthpiece (not shown) located at the edge of the device. Amongst the components not shown in FIG. 6 is the mechanism for supporting and advancing the cavity disc.

Associated with each cavity 33 is a lid member 35 which, in an initial state, seals the cavity via a sealing membrane 36. An air inlet 34 is provided in the casing 31 through which air is drawn when a patient inhales through the mouthpiece. Air flows through the device along a path shown by arrows B in FIG. 6. An air stream entering the device triggers the lifting of the lid member 35 associated with whichever cavity is in registry with the mouthpiece at that time. The triggering and lid lifting mechanisms are not shown in FIG. 6.

The lid member 35 on the left hand side of FIG. 6 is shown in the open position. It may be seen that the lid member 35 provides the upper wall, or ceiling, of a flow passage 37 which passes across the top of the now open cavity 33. The lower wall, or floor, of the flow passage is provided by an upper surface of the cavity disc 32. The side walls of the flow passage 37 are provided by the closed lid members 35 on each side of the open member 35. A closed lid member 35 is shown for example on the right side of FIG. 6, but it will be appreciated that there can be a number of these members 35 all around the circumference of the disc 32. In some embodiments, the side walls of the flow passages 37 may be provided by separate wall members (not shown) extending between the lid members 35.

As can be seen from the above description, a cavity 33 is opened essentially at the same time that a flow of air passes through the flow passage 37 across the opening of the cavity. A circulating airflow, represented highly schematically at 39, is induced in the cavity by the phenomenon of shear driven cavity flow. Powder 38 in the cavity is entrained in the circulating flow 39 during which time it is deaggregated, and then the deaggregated powder subsequently entrained in the flow through the flow passage 37 and then through the mouthpiece to the patient.

Each cavity is 4.5 mm long in the flow direction, 5 mm deep and (in plan view) is tapered in the flow direction, with an average width of 2.3 mm. It is filled with powder to a depth of 2.5 mm, leaving a 2.5 mm headspace. A large radius (2 mm) is provided on the upstream lower edge of the cavity to assist the development of a cylindrical circulating flow. A smaller 1 mm radius is provided on the downstream lower edge.

The device is intended to be used with the cavity openings facing upwards. However, since a cavity is only opened when there is already an airflow in the device and, it is believed that a circulating, shear driven flow is induced in the cavity before the powder has a chance to fall out of the cavity under gravity. It has been found that the performance of the device is largely independent of orientation.

In some embodiments, the cavities have the shape of Design B (see Example 4).

A fourth embodiment (not shown in the figures) includes a single inhalation device containing one cavity with medicament powder in a simple cylindrical plastic case with an inlet and a mouthpiece. The cavity has the same geometry as one of the cavities of the third embodiment, and the flow passage above the cavity has the same dimensions. The flow passage communicates with the air inlet and the mouthpiece. In place of a lid member, the cavity is sealed with a foil strip which extends outside the housing of the inhaler and may be removed by pulling.

The invention claimed is:

1. A dry powder inhaler device for dispensing an air stream carrying a dose of medicament powder, the device defining a flow passage and a powder storage cavity having a cavity opening, wherein the cavity opening is disposed in a wall of the flow passage with the flow passage arranged to direct a flow of air across the cavity opening, wherein the cavity opening has a length in the flow direction, and has a depth, the cavity opening length being between 50% and 150% of the cavity depth, and at least 80% of a maximum length of the cavity in the flow direction, and wherein the flow passage has a maximum height immediately adjacent the cavity, the maximum height being between 0.5 mm and 4 mm.

2. The device of claim 1, wherein the maximum height of the flow passage adjacent the cavity is between 0.5 mm and 3 mm.

3. The device of claim 2, wherein the maximum height of the flow passage adjacent the cavity is between 1 mm and 2 mm.

4. The device of claim 1, wherein the flow passage is arranged to create a substantially unidirectional flow across the cavity opening.

5. The device of claim 1, wherein the flow passage has a maximum width in the region of the cavity of between 2 mm and 6 mm.

6. The device of claim 1, wherein the cavity opening is generally of quadrilateral shape with fillet radii of 0.001 mm to 0.5 mm.

7. The device of claim 6, wherein the cavity opening has a rectangular or trapezoidal shape.

8. The device of claim 6, wherein the cavity opening has fillet radii of 0.01 mm to 0.3 mm.

9. The device of claim 6, wherein the cavity opening has an aspect ratio in the range 1.5 to 4.0.

10. The device of claim 9, wherein the cavity opening has an aspect ratio in the range of 1.8 to 3.5.

11. The device of claim 9, wherein the cavity opening has an aspect ratio in the range of 2.6 to 3.2.

12. The device of claim 1, wherein the length of the cavity opening in the flow direction is between 75% and 140% of the cavity depth.

13. The device of claim 12, wherein the length of the cavity opening in the flow direction is between 90% and 135% of the cavity depth.

14. The device of claim 1, wherein the cavity has a lower front or rear edge, with respect to the flow direction, with a radius of between 0.5 mm and 3 mm.

15. The device of claim 1, comprising a flow perturbing member projecting from a wall of the flow passage, the flow perturbing member being located with its most upstream extent between 1 mm and 20 mm upstream of the cavity.

16. The device of claim 15, wherein the flow perturbing member projects from a wall in which the cavity opening is formed.

17. The device of claim 1, further comprising a lid member associated with the cavity and movable between a first position in which the cavity is closed and a second position in which the cavity is open, wherein the lid member provides part of a boundary of the flow passage.

18. The device of claim 1, defining a second powder storage cavity that opens into the flow passage downstream of said cavity opening.

19. The device of claim 1, further comprising a plurality of flow passages arranged around the circumference of a circle, the flow passages being arranged such that the flow direction is radial with respect to the circle, at least one said powder storage cavity being located in each flow passage.

20. The device of claim 1 charged with medicament powder in the cavity.

21. The device of claim 20, wherein the medicament powder contains an active ingredient selected from the group consisting of mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propane-sulphonamide, hydrochloride, indacaterol, aclidinium bromide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof; N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof; a [2-(4-Chloro-benzyloxy)-ethyl]-[2-((R)-cyclohexyl-hydroxy-phenyl-methyl)-oxazol-5-ylmethyl]-dimethyl-ammonium salt; a (R)-1-[2-(4-Fluoro-phenyl)-ethyl]-3-((S)-2-phenyl-2-piperidin-1-yl-propionyloxy)-1-azonia-bicyclo[2.2.2]octane salt; and combinations thereof.

22. A replacement magazine configured to be received in a device as described in claim 1, the magazine comprising a cavity or cavities charged with medicament powder.

23. A device for dispensing an air stream carrying a dose of medicament powder, the device defining a flow passage and a powder storage cavity having a cavity opening disposed in a wall of the flow passage, the device comprising a lid member movable between a first position in which the cavity is closed and a second position in which the cavity is open and in which the lid member provides part of a boundary of the flow passage, wherein the flow passage is arranged to direct a flow of air across the cavity opening, wherein the cavity opening has a length in the flow direction of between 50% and 150% of a depth of the cavity, and wherein the flow passage has a maximum height adjacent the cavity of less than 4 mm.

24. The device of claim 23, defining a second powder storage cavity that opens into the flow passage, wherein the second cavity is also closed when the lid member is in the first position and open when the lid member is in the second position.

25. The device of claim 23 charged with medicament powder in the cavity or cavities.

26. The device of claim 25 wherein the medicament powder contains an active ingredient selected from the group consisting of mometasone, ipratropium bromide, tiotropium and salts thereof, salemeterol, fluticasone propionate, beclomethasone dipropionate, reproterol, clenbuterol, rofleponide and salts, nedocromil, sodium cromoglycate, flunisolide, budesonide, formoterol fumarate dihydrate, terbutaline, terbutaline sulphate, salbutamol base and sulphate, fenoterol, 3-[2-(4-Hydroxy-2-oxo-3H-1,3-benzothiazol-7-yl)ethylamino]-N-[2-[2-(4-methylphenyl)ethoxy]ethyl]propane-sulphonamide, hydrochloride, indacaterol, aclidinium bromide, N-[2-(Diethylamino)ethyl]-N-(2-{[2-(4-hydroxy-2-oxo-2,3-dihydro-1,3-benzothiazol-7-yl)ethyl]amino}ethyl)-3-[2-(1-naphthyl)ethoxy]propanamide or a pharmaceutically acceptable salt thereof; N-Cyclohexyl-$N^3$-[2-(3-fluorophenyl)ethyl]-N-(2-{[2-(4-hydroxy-2-oxo-2,3-dihydro-1,3-benzothiazol-7-yl)ethyl]amino}ethyl)-β-alaninamide or a pharmaceutically acceptable salt thereof; a [2-(4-Chloro-benzyloxy)-ethyl]-[2-((R)-cyclohexyl-hydroxy-phenyl-methyl)-oxazol-5-ylmethyl]-dimethyl-ammonium salt; a (R)-1-[2-(4-Fluoro-phenyl)-ethyl]-3-((S)-2-phenyl-2- piperidin-1-yl-propionyloxy)-1-azonia-bicyclo[2.2.2]octane salt; and combinations thereof.

27. A dry powder inhaler device for dispensing an air stream carrying a dose of medicament powder, the device defining a flow passage and a powder storage cavity having only a single cavity opening in a wall of the flow passage, with the flow passage arranged to direct a flow of air across the cavity opening,
   wherein the cavity opening has a length in the flow direction of between 50% and 150% of a depth of the cavity, and
   wherein the flow passage has a maximum height immediately adjacent the cavity of between 0.5 mm and 4 mm.

28. A cavity disc for a dry powder inhaler, the cavity disc defining a plurality of powder containing cavities arranged in a circular pattern on the disc, the cavities each having an trapezoid-shaped opening, a radial direction length of 50% to 150% of a depth of the cavity, and a flow passage having a maximum height immediately adjacent to the cavity being less than 4 mm.

29. The cavity disc of claim 28, wherein the trapezoid-shaped opening is covered by a removable seal or lid.

30. The cavity disc of claim 28, wherein the radial direction length of each cavity is at least 80% of a maximum length of the cavity in the radial direction.

31. The cavity disc of claim 28, wherein lower front or rear edges of each cavity, with respect to the flow direction, have a radius of between 0.5 mm and 3 mm.

32. A dry powder inhaler device for dispensing an air stream carrying a dose of medicament powder, the device defining a flow passage and a powder storage cavity having a cavity opening,
   wherein the cavity opening is disposed in a wall of the flow passage with the flow passage arranged to direct a flow of air across the cavity opening,
   wherein the cavity opening has a length in the flow direction, and has a depth, the cavity opening length being between 50% and 150% of the cavity depth, and
   wherein the flow passage has a maximum height immediately adjacent the cavity is at most 4 mm and the average surface shear stress over a lower half of the cavity is at least 0.5 Pa.

33. A dry powder inhaler device for dispensing an air stream carrying a dose of medicament powder, the device defining a flow passage and a powder storage cavity having a cavity opening,
   wherein the cavity opening is disposed in a wall of the flow passage with the flow passage arranged to direct a flow of air across the cavity opening,
   wherein the cavity opening has a length in the flow direction, and has a depth, the cavity opening length being between 50% and 150% of the cavity depth, and
   wherein the flow passage has a maximum height immediately adjacent the cavity is at most 3 mm and the average surface shear stress over a lower half of the cavity is at least about 1 Pa.

34. A device for dispensing an air stream carrying a dose of medicament powder, the device defining a flow passage and a powder storage cavity having a cavity opening disposed in a wall of the flow passage, the device comprising a lid member movable between a first position in which the cavity is closed and a second position in which the cavity is open and in which the lid member provides part of a boundary of the flow passage,
   wherein the flow passage is arranged to direct a flow of air across the cavity opening,
   wherein the cavity opening has a length in the flow direction of between 50% and 150% of a depth of the cavity, and
   wherein the flow passage has a maximum height adjacent the cavity is at most 4 mm and the average surface shear stress over a lower half of the cavity is at least 0.5 Pa.

35. A device for dispensing an air stream carrying a dose of medicament powder, the device defining a flow passage and a powder storage cavity having a cavity opening disposed in a wall of the flow passage, the device comprising a lid member movable between a first position in which the cavity is closed and a second position in which the cavity is open and in which the lid member provides part of a boundary of the flow passage,
   wherein the flow passage is arranged to direct a flow of air across the cavity opening,
   wherein the cavity opening has a length in the flow direction of between 50% and 150% of a depth of the cavity, and
   wherein the flow passage has a maximum height adjacent the cavity is at most 3 mm and the average surface shear stress over a lower half of the cavity is at least about 1 Pa.

* * * * *